United States Patent
Odedra et al.

(10) Patent No.: US 9,175,023 B2
(45) Date of Patent: Nov. 3, 2015

(54) MOLYBDENUM ALLYL COMPLEXES AND USE THEREOF IN THIN FILM DEPOSITION

(71) Applicant: SIGMA-ALDRICH CO. LLC, St. Louis, MO (US)

(72) Inventors: Rajesh Odedra, Altringham (GB); Shaun Garratt, Wirral (GB); Mark Saly, North Andover, MA (US); Ravi Kanjolia, North Andover, MA (US)

(73) Assignee: SIGMA-ALDRICH CO. LLC, St. Louis, MO (US)

( * ) Notice: Subject to any disclaimer, the term of this patent is extended or adjusted under 35 U.S.C. 154(b) by 0 days.

(21) Appl. No.: 14/374,289

(22) PCT Filed: Jan. 18, 2013

(86) PCT No.: PCT/US2013/022260
§ 371 (c)(1),
(2) Date: Jul. 24, 2014

(87) PCT Pub. No.: WO2013/112383
PCT Pub. Date: Aug. 1, 2013

(65) Prior Publication Data
US 2014/0370192 A1  Dec. 18, 2014

Related U.S. Application Data

(60) Provisional application No. 61/591,002, filed on Jan. 26, 2012, provisional application No. 61/711,770, filed on Oct. 10, 2012.

(51) Int. Cl.
*C07F 11/00* (2006.01)
*C23C 16/18* (2006.01)
*C23C 16/455* (2006.01)

(52) U.S. Cl.
CPC ............ *C07F 11/00* (2013.01); *C23C 16/18* (2013.01); *C23C 16/45553* (2013.01)

(58) Field of Classification Search
CPC .... C07F 11/00; C23C 16/18; C23C 16/45553
USPC ................... 556/58, 60; 427/255.6
See application file for complete search history.

(56) References Cited

U.S. PATENT DOCUMENTS

| | | | |
|---|---|---|---|
| 4,581,249 A | 4/1986 | Kamiya | |
| 5,064,686 A | 11/1991 | McGeary | |
| 6,698,728 B1 | 3/2004 | Ravetz et al. | |
| 7,282,119 B2 | 10/2007 | Odedra et al. | |
| 7,419,698 B2 | 9/2008 | Jones | |
| 7,927,661 B2 | 4/2011 | Jones | |
| 8,039,062 B2 | 10/2011 | Heys et al. | |
| 8,221,852 B2 | 7/2012 | Heys et al. | |
| 8,476,467 B2 | 7/2013 | Kanjolia et al. | |
| 8,481,121 B2 | 7/2013 | Kanjolia et al. | |
| 8,568,530 B2 | 10/2013 | Heys et al. | |
| 8,613,975 B2 | 12/2013 | Chalker et al. | |
| 2011/0021803 A1 | 1/2011 | Jin et al. | |

(Continued)

FOREIGN PATENT DOCUMENTS

| | | |
|---|---|---|
| TW | 200540291 | 12/2005 |
| WO | WO-2009/117583 A2 | 9/2009 |
| WO | WO-2009/143452 A1 | 11/2009 |
| WO | WO-2009/143458 A1 | 11/2009 |
| WO | WO-2009/155507 A1 | 12/2009 |
| WO | WO-2009/155520 A1 | 12/2009 |
| WO | WO-2013/112383 A1 | 8/2013 |

OTHER PUBLICATIONS

Allen et al., Journal of the Chemical Society, Dalton Transactions: Inorganic Chemistry (1972-1999), No. 6, pp. 1157-1169 (1984).*
International Preliminary Report on Patentability dated Jul. 29, 2014 issued in PCT Application No. PCT/US2013/022260.
Diskus, M., et al. (2011) "Growth of thin films of molybdenum oxide by atomic layer deposition", *Journal of Materials Chemistry*, 21:705-710.
Ellefson, C.A., et al. (2012) "Synthesis and applications of molybdenum (IV) oxide",*Journal of Mater. Science*, 47:2057-2071.
George, S.M., et al. (1996) "Surface chemistry for atomic layer growth", *J. Phys. Chem.*, 100:13121-13131.

(Continued)

*Primary Examiner* — Porfirio Nazario Gonzalez
(74) *Attorney, Agent, or Firm* — Harness, Dickey & Pierce, P.L.C.

(57) ABSTRACT

Molybdenum complexes and use thereof in thin film deposition, such as CVD and ALD are provided herein. The molybdenum complexes correspond in structure to Formula (I) and Formula (II), wherein $R^1$, $R^3$, $R^5$, $R^7$, $R^8$ and $R^{10}$ are independently and at each occurrence alkyl; $R^2$, $R^6$ and $R^9$ are independently alkyl; $R^4$ and $R^{11}$ are independently and at each occurrence selected from the group consisting of alkyl, alkenyl, and alkynyl; x, z, a, c, d and f are independently zero, 1, or 2; y, b and e are independently zero or 1; and n and m are independently zero to 5.

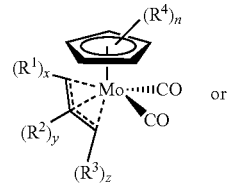

Formula I

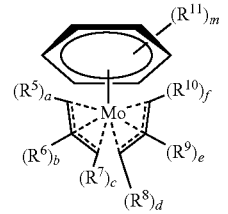

Formula II

7 Claims, 29 Drawing Sheets

(56) References Cited

U.S. PATENT DOCUMENTS

| | | |
|---|---|---|
| 2011/0151227 A1 | 6/2011 | Chalker et al. |
| 2011/0165780 A1 | 7/2011 | Kanjolia et al. |
| 2011/0184156 A1 | 7/2011 | Jones |
| 2012/0177845 A1 | 7/2012 | Odedra et al. |
| 2012/0178266 A1 | 7/2012 | Heys et al. |
| 2013/0041170 A1 | 2/2013 | Odedra et al. |
| 2013/0052368 A1 | 2/2013 | Rushworth et al. |
| 2013/0196065 A1 | 8/2013 | Heys et al. |

OTHER PUBLICATIONS

Green, J., et al. (1997) "Cyclopentadienyltris(dimethylamido)molybdenum: photoelectron spectroscopy, electron diffraction and theoretical calculations", *Journal of the Chemical Society, Dalton Transactions*, No. 8: 3219-3224.

Green, M.L.H., et al. (1973) "Arene molybdenum chemistry: arene(π-allyl)molybdenum derivatives containing carboxylate, aminocarboxylate, and related ligands", *Journal of Chem. Soc., Dalton Transactions*, 1403-1408.

Green, M.L.H., et al. (1973) "Arene molybdenum chemistry: some bis-π-allylic derivatives", *Journal of Chem. Soc., Dalton Transactions*, 1952-1954.

International Search Report and Written Opinion dated Mar. 20, 2013 issued in PCT Application No. PCT/US2013/022260.

Miikkulainen, V., et al. (2007) "Atomic later deposition of molybdenum nitride from bis(tert-butylimido)-bis(dimethylamido)molybdenum and ammonia onto several types of substrate materials with equal growth per cycle", *Chem. Mater.*, 19:263-269.

Potter, R.J., et al. (2005) "Deposition of $HfO_2$, $Gd_2O_3$ and $PrO_x$ by liquid injection ALD techniques", *Chem. Vap. Deposition*, 11(3):159-169.

Theopold, K.H., et al. (2003) "Product class 5: Organometallic π-complexes if chromium, molybdenum, and tungsten excluding arene", *Science of Synthesis*, 229-281.

\* cited by examiner

A.

B.

A.

B.

A.

B.

A.

B.

MOLYBDENUM ALLYL COMPLEXES AND USE THEREOF IN THIN FILM DEPOSITION

CROSS-REFERENCE TO RELATED APPLICATIONS

This application is a national stage application of International Patent Application No. PCT/US2013/022260 filed on 18 Jan. 2013, which claims priority to U.S. Provisional Patent Application Ser. Nos. 61/591,002 filed on 26 Jan. 2012 and 61/711,770 filed on 10 Oct. 2012, the entire disclosures of which are each hereby incorporated by reference for all purposes in their entireties.

FIELD OF THE INVENTION

The present invention relates to molybdenum (Mo) complexes and methods of preparing thin films by chemical vapor deposition (CVD) or atomic layer deposition (ALD) using such complexes.

BACKGROUND OF THE INVENTION

Various organometallic precursors are used to form thin metal films. A variety of techniques have been used for the deposition of thin films. These include reactive sputtering, ion-assisted deposition, sol-gel deposition, CVD (also known as metalorganic CVD or MOCVD), and ALD (also known as atomic layer epitaxy). The CVD and ALD processes are being increasingly used as they have the advantages of good compositional control, high film uniformity, good control of doping, and, significantly, they give excellent conformal step coverage on highly non-planar microelectronics device geometries.

CVD is a chemical process whereby precursors are used to form a thin film on a substrate. In a typical CVD process, the precursors are passed over a substrate (e.g., a wafer) in a low pressure or ambient pressure reaction chamber. The precursors react and/or decompose on the substrate surface creating a thin film of deposited material. Volatile by-products are removed by gas flow through the reaction chamber. The deposited film thickness can be difficult to control because it depends on coordination of many parameters such as temperature, pressure, gas flow volumes and uniformity, chemical depletion effects, and time.

ALD is also a method for the deposition of thin films. It is a self-limiting, sequential, unique film growth technique based on surface reactions that can provide precise thickness control and deposit conformal thin films of materials provided by precursors onto substrates of varying compositions. In ALD, the precursors are separated during the reaction. The first precursor is passed over the substrate producing a monolayer on the substrate. Any excess unreacted precursor is pumped out of the reaction chamber. A second precursor is then passed over the substrate and reacts with the first precursor, forming a second monolayer of film over the first-formed monolayer of film on the substrate surface. This cycle is repeated to create a film of desired thickness. ALD film growth is self-limiting and based on surface reactions, creating uniform depositions that can be controlled at the nanometer-thickness scale.

Thin films have a variety of important applications, such as nanotechnology and fabrication of semiconductor devices. Examples of such applications include, conductive films, high-refractive index optical coatings, corrosion-protection coatings, photocatalytic self-cleaning glass coatings, biocompatible coatings, dielectric capacitor layers and gate dielectric insulating films in field-effect transistors (FET), capacitor electrodes, gate electrodes, adhesive diffusion barriers and integrated circuits. Thin films are also used in microelectronics applications, such as the high-κ dielectric oxide for dynamic random access memory (DRAM) applications and the ferroelectric perovskites used in infra-red detectors and non-volatile ferroelectric random access memories (NV-FeRAMs). The continual decrease in the size of microelectronics components has increased the need for the use of such thin films.

Oxides and nitrides of molybdenum have numerous important applications. For example, molybdenum dioxide ($MoO_2$) displays unusual metal-like conductivity and has found applications in hydrocarbon oxidation catalysts, solid oxide fuel cell (SOFC) anodes, and high capacity reversible lithium ion battery (LIB) anodes. See, for example, Ellefson, C. A., et al., *J. Mater. Sci.* 2012, 47, 2057-2071. Molybdenum trioxide ($MoO_3$) exhibits interesting electrochromic and catalytic properties and has found applications in nano-structured gas sensors and in solid-state lithium ion batteries. See, for example, Diskus, M., et al., *J. Mater. Chem.* 2011, 21, 705-710. Finally, thin films of transition metal nitrides have long been known to generally possess good mechanical and chemical stability. Films of molybdenum nitride (MoN and/or $Mo_2N$) have been studied for applications including microelectronic diffusion barriers, high-$T_c$ superconductors, and tribological and protective coatings. See, for example, Miikkulainen, V., et al., *Chem. Mater.* 2007, 19, 263-269.

Theopold, K. H., et al. report the synthesis and isolation of the Mo complex $CpMo(CO)_2(\eta^3\text{-}2\text{-methylallyl})$. *Science of Synthesis*, 2003, 229-281.

Green, J., et al. report the synthesis and isolation of the Mo complex, $(C_6H_6)Mo(\eta^3\text{-allyl})_2$. *J. Chem. Soc., Dalton Trans.* 1973, 1403-1408 and *J. Chem. Soc., Dalton Trans.* 1973, 1952-1954.

Current molybdenum precursors for use in CVD and ALD do not provide the required performance to implement new processes for fabrication of next generation devices, such as semiconductors. For example, improved thermal stability, higher volatility, increased vapor pressures, and increased deposition rates are needed.

SUMMARY OF THE INVENTION

In one embodiment, an organometallic complex corresponding in structure to Formula I is provided:

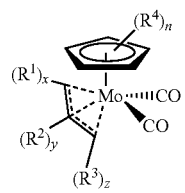

Formula I wherein $R^1$ and $R^3$ are independently and at each occurrence alkyl; $R^2$ is alkyl; $R^4$ is independently and at each occurrence selected from the group consisting of alkyl, alkenyl, and alkynyl; x and z are independently zero, 1, or 2; y is zero or 1; and n is zero to 5.

In another embodiment, an organometallic complex corresponding in structure to Formula II is provided:

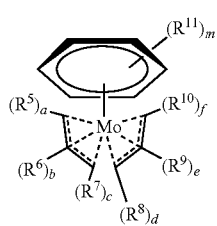

Formula II wherein $R^5$, $R^7$, $R^8$, and $R^{10}$, are independently and at each occurrence alkyl; $R^6$ and $R^9$ are independently alkyl; $R^{11}$ is independently and at each occurrence selected from the group consisting of alkyl, alkenyl, and alkynyl; a, c, d, and f are independently zero, 1, or 2; b and e are independently zero or 1; and m is zero to 6.

Methods for forming molybdenum-containing films by vapor deposition processes, such as CVD and ALD, are provided herein using organometallic complexes according to Formula I and/or Formula II herein.

Other embodiments, including particular aspects of the embodiments summarized above, will be evident from the detailed description that follows.

DETAILED DESCRIPTION OF THE INVENTION

Figure 1:
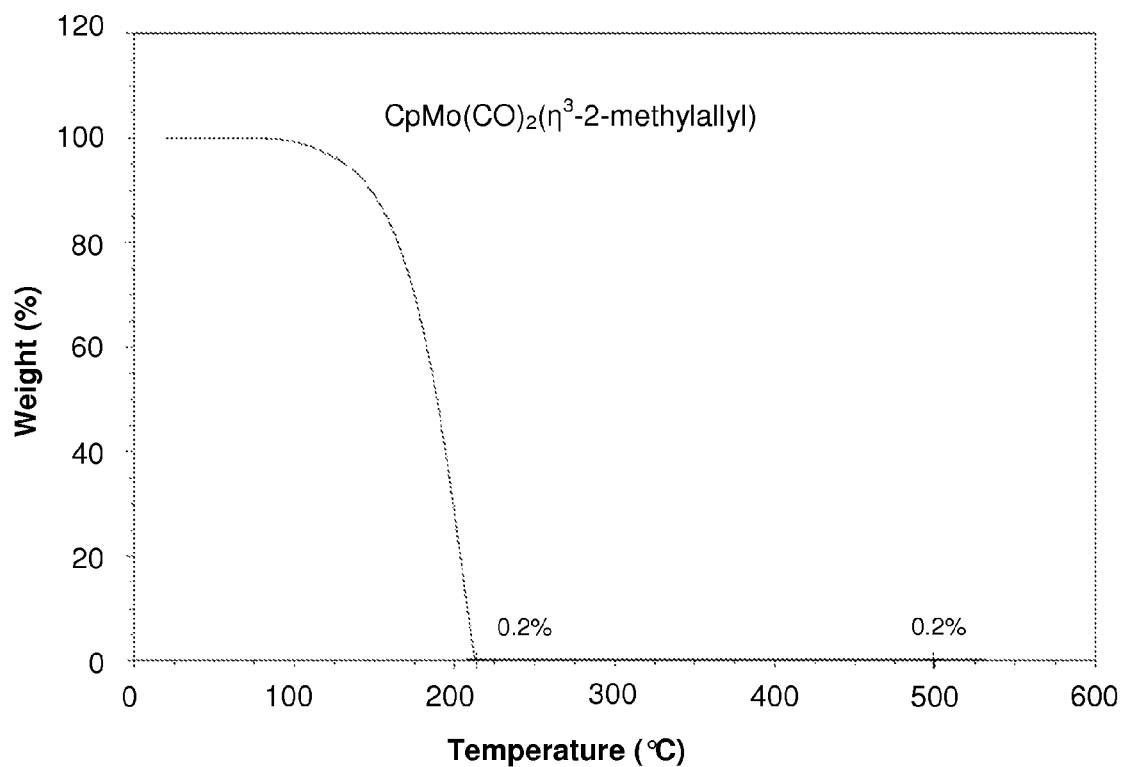
FIG. 1 is a graphical representation of thermal gravimetric analysis (TGA) data demonstrating % weight loss vs. temperature of CpMo(CO)$_2$($\eta^3$-2-methylallyl).

In various aspects of the invention, Mo (II) complexes, methods of making such complexes, and methods of using such complexes to form Mo, MoN, $Mo_2N$, $MoN/Mo_2N$, $MoO_2$, $MOO_3$, and $MoO_2/MoO_3$ films are provided.

In one embodiment, the methods of the invention can be used to create or grow Mo-containing thin films which display conductive properties.

As used herein, the term "precursor" refers to an organometallic molecule, complex and/or compound which is passed over a substrate to form a thin film by a deposition process, for example, by CVD or ALD.

As used herein, the term "vapor deposition process" is used to refer to any type of vapor deposition technique such as CVD or ALD. In various embodiments of the invention, CVD may take the form of conventional (i.e., continuous flow) CVD, liquid injection CVD, or photo-assisted CVD. CVD may also take the form of a pulsed technique, i.e., pulsed CVD. In other embodiments, ALD may take the form of conventional (i.e., pulsed injection) ALD, liquid injection ALD, photo-assisted ALD, or plasma-assisted ALD. The term "vapor deposition process" further includes various vapor deposition techniques described in *Chemical Vapour Deposition: Precursors, Processes, and Applications*; Jones, A. C.; Hitchman, M. L., Eds. The Royal Society of Chemistry: Cambridge, 2009; Chapter 1, pp 1-36.

The term "Cp" refers to a cyclopentadienyl ($C_5H_5$) ligand which is bound to molybdenum. As used herein, all five carbon atoms of the Cp ligand are bound to the metal center in $\eta^5$-coordination by π bonding, therefore the complexes of the invention are π complexes.

The term "allyl" refers to an allyl ($C_3H_5$) ligand which is bound to molybdenum. As used herein, the allyl ligand has a resonating double bond and all three carbon atoms of the allyl ligand are bound to the metal center in $\eta^3$-coordination by π bonding. Therefore, the complexes of the invention are π complexes. Both of these features are represented by the dashed bonds. When the allyl portion is substituted by one $R^1$ group, the $R^1$ group replaces an allylic hydrogen to become $[R^1C_3H_4]$; when substituted with two R groups $R^1$ and $R^2$, it becomes $[R^1R^2C_3H_3]$ where $R^1$ and $R^2$ are the same or different, and so forth.

The term "alkyl" refers to a saturated hydrocarbon chain of 1 to about 8 carbon atoms in length, such as, but not limited to, methyl, ethyl, propyl and butyl. The alkyl group may be straight-chain or branched-chain. "Alkyl" is intended to embrace all structural isomeric forms of an alkyl group. For example, as used herein, propyl encompasses both n-propyl and isopropyl; butyl encompasses n-butyl, sec-butyl, isobutyl and tert-butyl. Further, as used herein, "Me" refers to methyl, and "Et" refers to ethyl, "i-Pr" refers to isopropyl, "t-Bu" refers to tert-butyl, and "Np" refers to neopentyl. It should also be noted that $C_2$ is intended to refer to an ethyl group, and not dimethyl.

Deposition of Mo metal, molybdenum nitrides such as MoN and $Mo_2N$ (or mixtures of such molybdenum nitrides), and molybdenum oxides such as $MoO_2$ and $MoO_3$ (or mixtures of such molybdenum oxides) is difficult to achieve due to stability issues, being either unstable or too stable for deposition. The organometallic complexes disclosed in the embodiments of the invention allow for control of physical properties as well as provide for increased stability and simple high yield synthesis.

In a first embodiment, an organometallic complex is provided corresponding in structure to Formula I:

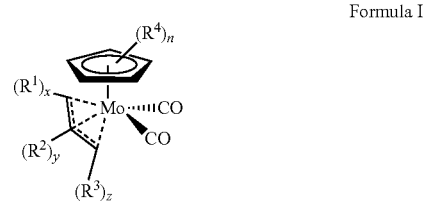

Formula I wherein $R^1$ and $R^3$ are independently and at each occurrence alkyl; $R^2$ is alkyl; $R^4$ is independently and at each occurrence selected from the group consisting of alkyl, alkenyl, and alkynyl; x and z are independently zero, 1, or 2; y is zero or 1; and n is zero to 5.

As used herein, the variables, x, y, z, and n are used to represent how many particular R substituents are attached to the appropriate carbon.

$R^1$, $R^2$, $R^3$, and $R^4$, at each occurrence, can be the same or different.

In one embodiment, if more than one $R^1$, $R^3$ or $R^4$ is present, than each occurrence of $R^1$, $R^3$ or $R^4$ can be the same or different. For example, the variable "x" can be two and both a methyl and an ethyl can be substituted on the appropriate carbon in Formula I. In other embodiments, each occurrence of $R^1$, $R^3$ or $R^4$ may be the same. For example, the variable "x" can be two and two methyl groups can be substituted on the appropriate carbon in Formula I, and so forth.

In one embodiment, $R^1$, $R^2$, $R^3$, and $R^4$ are independently at each occurrence $C_1$-$C_8$-alkyl. In some such embodiments, $R^1$, $R^2$, $R^3$, and $R^4$ are independently at each occurrence $C_1$-$C_4$-alkyl.

In another embodiment, $R^1$, $R^2$, $R^3$, and $R^4$ are independently at each occurrence $C_2$-$C_8$-alkyl.

In another embodiment, $R^1$, $R^2$, $R^3$, and $R^4$ are independently at each occurrence $C_3$-$C_8$-alkyl.

In another embodiment, $R^1$, $R^2$, $R^3$, and $R^4$ are independently at each occurrence $C_4$-$C_8$-alkyl.

In another embodiment, $R^1$, $R^2$, $R^3$, and $R^4$ are independently at each occurrence $C_5$-$C_8$-alkyl.

In another embodiment, $R^1$, $R^2$, and $R^3$ are independently at each occurrence $C_2$-$C_7$-alkyl or $C_3$-$C_7$-alkyl or $C_4$-$C_7$-alkyl and $R^4$ is $C_1$-$C_7$-alkyl. In a further embodiment, $R^4$ is $C_2$-$C_7$-alkyl. In another embodiment, $R^4$ is $C_3$-$C_7$-alkyl. In a further embodiment, $R^4$ is $C_4$-$C_7$-alkyl.

In one embodiment, $R^1$, $R^2$, $R^3$ are independently at each occurrence alkyl; $R^4$ is selected from the group consisting of alkyl, alkenyl, and alkynyl; x and z are independently zero, 1, or 2; y is zero or 1; and n is zero to 5, wherein when n is zero, $R^1$ or $R^2$ or $R^3$, if present, is $C_2$-$C_8$-alkyl; and when n is 1, $R^1$ or $R^3$, if present, is $C_2$-$C_8$-alkyl.

In one embodiment, $R^1$, $R^2$, and/or $R^3$ is methyl, and $R^4$ is methyl, ethyl, propyl, or butyl, and n is zero, 1, or 2.

In another embodiment, $R^1$, $R^2$, and/or $R^3$ is ethyl, and $R^4$ is methyl, ethyl, propyl, or butyl, and n is zero, 1, or 2.

In another embodiment, $R^1$, $R^2$, and/or $R^3$ is propyl, and $R^4$ is methyl, ethyl, propyl, or butyl, and n is zero, 1, or 2. Therefore, $R^1$, $R^2$ and/or $R^3$ may be n-propyl or isopropyl.

In another embodiment, $R^1$, $R^2$, and/or $R^3$ is butyl, and $R^4$ is methyl, ethyl, propyl, or butyl, and n is zero, 1, or 2. Therefore, $R^1$, $R^2$, and/or $R^3$ may be n-butyl, sec-butyl, isobutyl, or tert-butyl. In a particular embodiment, $R^1$, $R^2$, and/or $R^3$ is tert-butyl.

In another embodiment, $R^1$, $R^2$, $R^3$, and/or $R^4$ is pentyl. Therefore, $R^1$, $R^2$, $R^3$, and/or $R^4$ may be neopentyl, straight-chained, or isopentyl. In another embodiment, $R^1$, $R^2$ and/or $R^3$ is neopentyl.

In another embodiment, $R^1$, $R^2$, $R^3$, and/or $R^4$ is hexyl.
In another embodiment, $R^1$, $R^2$, $R^3$, and/or $R^4$ is heptyl.
In another embodiment, $R^1$, $R^2$, $R^3$, and/or $R^4$ is octyl.
In one embodiment, x and z are independently zero, 1, or 2.
In one embodiment, y is zero or 1.
In another embodiment, y is one, and x and z are each zero.
In another embodiment, x is one, and y and z are each zero.
In another embodiment, at least two of x, y, and z are one.
In another embodiment, x, y, and z are each one.
In one embodiment, n is zero, 1, 2, 3, 4, or 5.
In another embodiment n is zero, 1, 2, or 3.
In another embodiment n is 1 or 2.
In another embodiment, n is zero or 1.
In another embodiment, n is 2, 3, 4, or 5.

Examples of organometallic complexes corresponding in structure to Formula I include

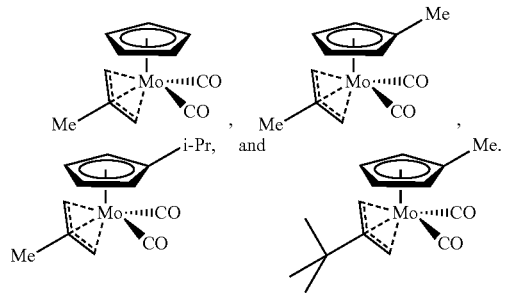

In another embodiment, an organometallic complex is provided corresponding in structure to Formula II:

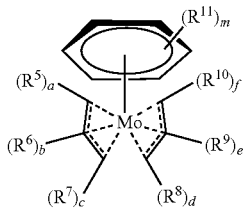

Formula II wherein $R^5$, $R^7$, $R^8$, and $R^{10}$, are independently and at each occurrence alkyl; $R^6$ and $R^9$ are independently alkyl; $R^{11}$ is independently and at each occurrence selected from the group consisting of alkyl, alkenyl, and alkynyl; a, c, d, and f are independently zero, 1, or 2; b and e are independently zero or 1; and m is zero to 6.

As used herein, the variables, a, b, c, d, e, f, and m are used to represent how many particular R substituents are attached to the appropriate carbon.

$R^5$, $R^6$, $R^7$, $R^8$, $R^9$, $R^{10}$, and $R^{11}$ can be the same or different.

In one embodiment, if more than one $R^5$, $R^7$, $R^8$, $R^{10}$, and $R^{11}$ is present, than each occurrence of $R^5$, $R^7$, $R^8$, $R^{10}$, and $R^{11}$ can be the same or different. For example, the variable "a" can be two and both a methyl and an ethyl can be substituted on the appropriate carbon in Formula II. In other embodiments, each occurrence of $R^5$, $R^7$, $R^8$, $R^{10}$, and $R^{11}$ may be the same. For example, the variable "a" can be two and two methyl groups can be substituted on the appropriate carbon in Formula II, and so forth.

In one embodiment, $R^5$, $R^6$, $R^7$, $R^8$, $R^9$, $R^{10}$, and $R^{11}$ are independently at each occurrence $C_1$-$C_8$-alkyl. In some such embodiments, $R^5$, $R^6$, $R^7$, $R^8$, $R^9$, $R^{10}$, and $R^{11}$ are independently at each occurrence $C_1$-$C_4$-alkyl.

In another embodiment, $R^5$, $R^6$, $R^7$, $R^8$, $R^9$, $R^{10}$, and $R^{11}$ are independently at each occurrence $C_2$-$C_8$-alkyl.

In another embodiment, $R^5$, $R^6$, $R^7$, $R^8$, $R^9$, $R^{10}$, and $R^{11}$ are independently at each occurrence $C_3$-$C_8$-alkyl.

In another embodiment, $R^5$, $R^6$, $R^7$, $R^8$, $R^9$, $R^{10}$, and $R^{11}$ are independently at each occurrence $C_4$-$C_8$-alkyl.

In another embodiment, $R^5$, $R^6$, $R^7$, $R^8$, $R^9$, $R^{10}$, and $R^{11}$ are independently at each occurrence $C_5$-$C_8$-alkyl.

In another embodiment, $R^5$, $R^6$, $R^7$, $R^8$, $R^9$, $R^{10}$ and $R^{11}$ are independently at each occurrence $C_1$-$C_7$-alkyl.

In another embodiment, $R^5$, $R^6$, $R^7$, $R^8$, $R^9$, $R^{10}$, and $R^{11}$ are independently at each occurrence $C_3$-$C_7$-alkyl.

In another embodiment, $R^5$, $R^6$, $R^7$, $R^8$, $R^9$, $R^{10}$, and $R^{11}$ are independently at each occurrence $C_4$-$C_7$-alkyl.

In one embodiment, $R^5$, $R^7$, $R^8$, and $R^{10}$, are independently and at each occurrence alkyl; $R^6$ and $R^9$ are independently alkyl; $R^{11}$ is independently and at each occurrence selected from the group consisting of alkyl, alkenyl, and alkynyl; a, c, d, and f are independently zero, 1, or 2; b and e are independently zero or 1; and m is zero to 6, wherein when m is zero, at least one of a, b, c, d, e, or f is 1 or 2; and when m is 1, $R^{11}$ is $C_2$-$C_8$-alkyl, alkenyl, or alkynyl.

In one embodiment, $R^5$, $R^6$, $R^7$, $R^8$, $R^9$, and/or $R^{10}$ is methyl, and $R^{11}$ is methyl, ethyl, propyl, or butyl, and m is zero, 1, 2, 3, or 4. In a more particular embodiment, m is 1, 2, 3, or 4.

In another embodiment, $R^5$, $R^6$, $R^7$, $R^8$, $R^9$, and/or $R^{10}$ is ethyl, and $R^{11}$ is methyl, ethyl, propyl, or butyl, and m is zero, 1, 2, 3, or 4. In a more particular embodiment, m is 1, 2, 3, or 4.

In another embodiment, $R^5$, $R^6$, $R^7$, $R^8$, $R^9$, and/or $R^{10}$ is propyl, and $R^{11}$ is methyl, ethyl, propyl, or butyl, and m is zero, 1, 2, 3, or 4. Therefore, $R^5$, $R^6$, $R^7$, $R^8$, $R^9$, and/or $R^{10}$ may be n-propyl, or isopropyl. In a more particular embodiment, m is 1, 2, 3, or 4.

In another embodiment, $R^5$, $R^6$, $R^7$, $R^8$, $R^9$, and/or $R^{10}$ is butyl, and $R^{11}$ is methyl, ethyl, propyl, or butyl, and m is zero, 1, 2, 3, or 4. Therefore, $R^5$, $R^6$, $R^7$, $R^8$, $R^9$, and/or $R^{10}$ may be n-butyl, sec-butyl, isobutyl, or tert-butyl. In a particular embodiment, $R^5$, $R^6$, $R^7$, $R^8$, $R^9$, and/or $R^{10}$ is tert-butyl. In a more particular embodiment, m is 1, 2, 3, or 4.

In another embodiment, $R^5$, $R^6$, $R^7$, $R^8$, $R^9$, $R^{10}$, and/or $R^{11}$ is pentyl. Therefore, $R^5$, $R^6$, $R^7$, $R^8$, $R^9$, and/or $R^{10}$ may be neopentyl, straight-chained, or isopentyl. In a particular embodiment, $R^5$, $R^6$, $R^7$, $R^8$, $R^9$, and/or $R^{10}$ is neopentyl.

In another embodiment, $R^5$, $R^6$, $R^7$, $R^8$, $R^9$, $R^{10}$, and/or $R^{11}$ is hexyl.

In another embodiment, $R^5$, $R^6$, $R^7$, $R^8$, $R^9$, $R^{10}$, and/or $R^{11}$ is heptyl.

In another embodiment, $R^5$, $R^6$, $R^7$, $R^8$, $R^9$, $R^{10}$, and/or $R^{11}$ is octyl.

In one embodiment, a, c, d, and f are independently zero, 1, or 2.

In one embodiment, b and e are independently zero or 1.

In another embodiment, a, c, d, and f are zero.

In another embodiment, a, b, c, d, e, and f are zero.

In another embodiment, a, c, d, and f are zero, and b and e are 1.

In another embodiment, at least two of a, b, and c are one, and at least two of d, e, and f are one.

In another embodiment, a, b, c, d, e, and f are each one.

In one embodiment, m is zero, 1, 2, 3, 4, 5, or 6, more particularly, m is zero, 1, 2, 3, or 4, and even more particularly, m is 1, 2, 3, or 4.

In another embodiment, m is zero, 1, or 3.

In another embodiment, the organometallic complex of Formula II corresponds in structure to Formula II(a):

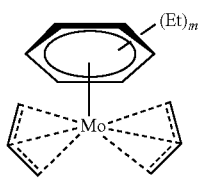

Formula II(a)

where m is as defined above. In a particular embodiment, m is zero, 1, 2, 3, or 4; in a more particular embodiment, m is 1, 2, 3, or 4.

In another embodiment, the organometallic complex of Formula II corresponds in structure to Formula II(b):

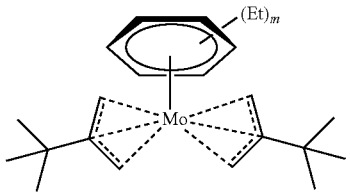

Formula II(b)

where m is as defined above. In a particular embodiment, m is zero, 1, 2, 3, or 4; in a more particular embodiment, m is 1, 2, 3, or 4.

Examples of organometallic complexes corresponding in structure to Formula II are shown in Table 1.

TABLE 1

Complexes of Formula II

II-1-a,

II-2-a,

II-3-a,

II-4-a,

II-5-a,

II-6-a,

II-7-a,

TABLE 1-continued
Complexes of Formula II
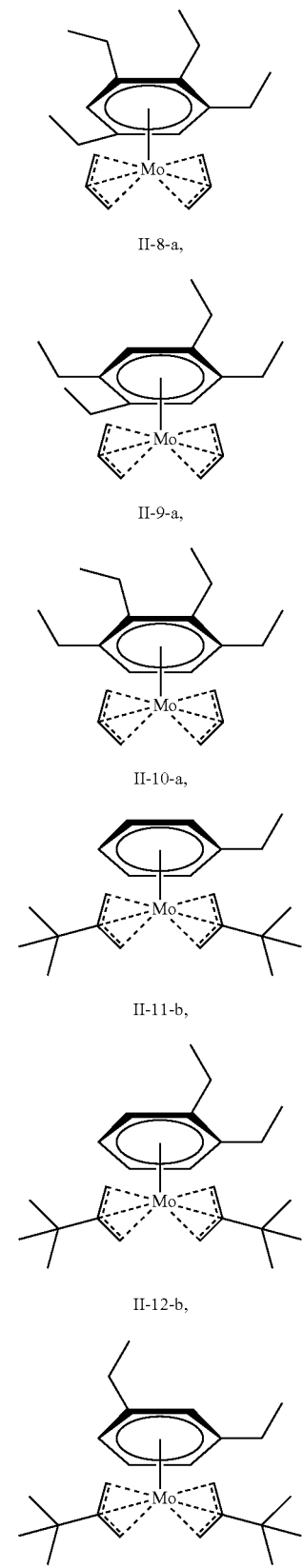
II-8-a,
II-9-a,
II-10-a,
II-11-b,
II-12-b,
TABLE 1-continued
Complexes of Formula II
II-13-b,
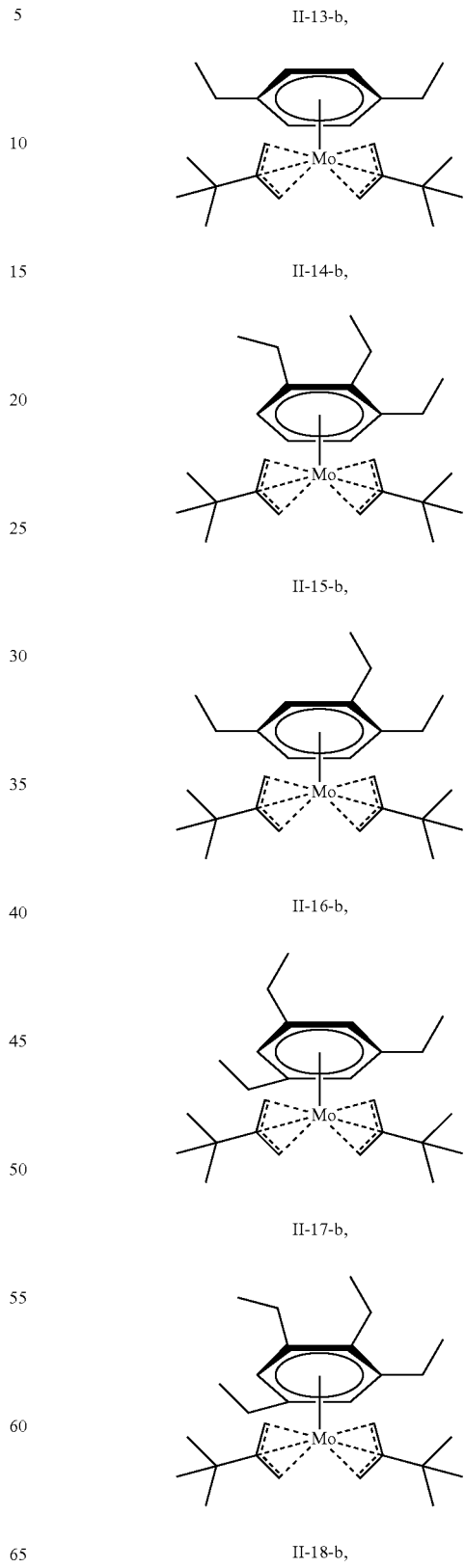
II-14-b,
II-15-b,
II-16-b,
II-17-b,
II-18-b, TABLE 1-continued Complexes of Formula II

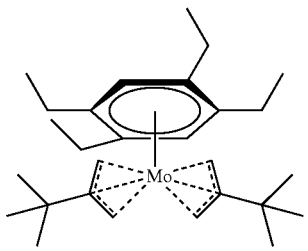

II-19-b,

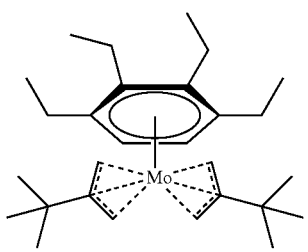

II-20-b,

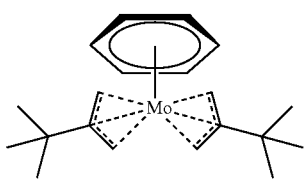

II-21-b,

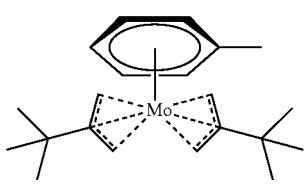

II-22,

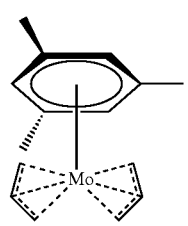

II-23,

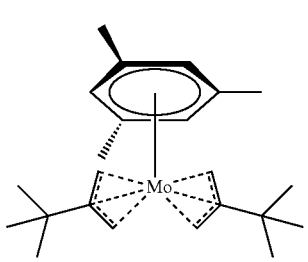

II-24,

TABLE 1-continued

Complexes of Formula II

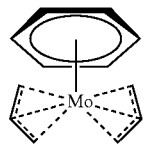

II-25-a, and

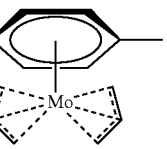

II-26.

In one embodiment, a mixture of two or more organometallic complexes of Formula II is provided.

In a particular embodiment, a mixture and/or combination of two or more organometallic complexes of Formula II(a) is provided.

In another particular embodiment, a mixture and/or combination of two or more organometallic complexes of Formula II(b) is provided.

In another embodiment, a mixture and/or combination of two or more organometallic complexes of Formula I and II is provided.

In another embodiment, a method of forming a molybdenum-containing film by a vapor deposition process is provided. The method comprises vaporizing at least one organometallic complex corresponding in structure to Formula I, Formula II, or a combination thereof, as disclosed herein. For example, this may include (1) vaporizing the at least one complex and (2) delivering the at least one complex to a substrate surface or passing the at least one complex over a substrate (and/or decomposing the at least one complex on the substrate surface).

In a particular embodiment, the organometallic complexes may be dissolved in an appropriate hydrocarbon or amine solvent. Appropriate hydrocarbon solvents include, but are not limited to aliphatic hydrocarbons, such as hexane, heptane, and nonane; aromatic hydrocarbons, such as toluene and xylene; aliphatic and cyclic ethers, such as diglyme, triglyme, and tetraglyme. Examples of appropriate amine solvents include, without limitation, octylamine and N,N-dimethyldodecylamine. For example, the organometallic complex may be dissolved in toluene to yield a solution with a concentration of about 0.05 M to about 1 M.

In another embodiment, at least one complex corresponding in structure to Formula I or Formula II may be delivered "neat" (undiluted by a carrier gas) to a substrate.

In one embodiment, the vapor deposition process is chemical vapor deposition.

In another embodiment, the vapor deposition process is atomic layer deposition.

The ALD and CVD methods of the invention encompass various types of ALD and CVD processes such as, but not limited to, continuous or pulsed injection processes, liquid injection processes, photo-assisted processes, and plasma-assisted processes. For purposes of clarity, the methods of the present invention specifically include direct liquid injection processes. For example, in direct liquid injection CVD ("DLI-CVD"), a solid or liquid complex may be dissolved in a suitable solvent and the solution formed therefrom injected into a vaporization chamber as a means to vaporize the complex. The vaporized complex is then transported/delivered to the substrate. In general, DLI-CVD may be particularly useful in those instances where a complex displays relatively low volatility or is otherwise difficult to vaporize.

In one embodiment, conventional or pulsed injection CVD is used to form a molybdenum-containing thin film by vaporizing and/or passing at least one complex according to Formula I and/or Formula II as disclosed herein over a substrate. For conventional and pulsed CVD processes see, for example, Smith, Donald (1995). *Thin-Film Deposition: Principles and Practice*. McGraw-Hill.

In one embodiment, CVD growth conditions for complexes according to Formula I and/or Formula II include, but are not limited to:

| | | |
|---|---|---|
| (1) | Substrate temperature: | 50-600° C. |
| (2) | Evaporator temperature (Mo source temp): | 0-200° C. |
| (3) | Reactor pressure: | 0-100 Torr |
| (4) | Argon or nitrogen carrier gas flow rate: | 0-500 sccm |
| (5) | Oxygen flow rate: | 0-500 sccm |
| (6) | Hydrogen flow rate: | 0-500 sccm |
| (7) | Run time: | will vary according to desired film thickness |

In another embodiment, photo-assisted CVD is used to form a molybdenum containing thin film by vaporizing and/or passing at least one complex according to Formula I and/or Formula II as disclosed herein over a substrate.

In a further embodiment, conventional (i.e., pulsed injection) ALD is used to form a molybdenum-containing thin film by vaporizing and/or passing at least one complex according to Formula I and/or Formula II as disclosed herein over a substrate. For conventional ALD processes see, for example, George S. M., et al., *J. Phys. Chem.*, 1996, 100, 13121-13131.

In another embodiment, liquid injection ALD is used to form a molybdenum-containing thin film by vaporizing and/or passing at least one complex according to Formula I and/or Formula II as disclosed herein over a substrate, wherein at least one liquid complex is delivered to the reaction chamber by direct liquid injection as opposed to vapor draw by a bubbler. For liquid injection ALD process see, for example, Potter R. J., et al., *Chem. Vap. Deposition*, 2005, 11(3), 159-169.

Examples of ALD growth conditions for complexes according to Formula I and/or Formula II include, but are not limited to:

| | | |
|---|---|---|
| (1) | Substrate temperature: | 0-400° C. |
| (2) | Evaporator temperature (Mo source temp): | 0-200° C. |
| (3) | Reactor pressure: | 0-100 Torr |
| (4) | Argon or nitrogen carrier gas flow rate: | 0-500 sccm |
| (5) | Reactive gas flow rate: | 0-500 sccm |
| (6) | Pulse sequence (complex/purge/reactive gas/purge): | will vary according to chamber size |
| (7) | Number of cycles: | will vary according to desired film thickness |

In another embodiment, photo-assisted ALD is used to form a molybdenum-containing thin film by vaporizing and/or passing at least one complex according to Formula I and/or Formula II as disclosed herein over a substrate. For photo-assisted ALD processes see, for example, U.S. Pat. No. 4,581,249.

In another embodiment, plasma-enhanced ALD is used to form molybdenum-containing thin films by vaporizing and/or passing at least one complex according to Formula I and/or Formula II as disclosed herein over a substrate.

Thus, the organometallic complexes according to Formula I or Formula II disclosed herein utilized in these methods may be liquid, solid, or gaseous. Typically, the organometallic complexes are liquids or low-melting solids at ambient temperatures with a vapor pressure sufficient to allow for consistent transport of the vapor to the process chamber. In some embodiments, the organometallic complex according to Formula I or Formula II is a solid with a melting point less than or equal to about 50° C., less than or equal to about 45° C., less than or equal to about 40° C., less than or equal to about 35° C., less than or equal to about 30° C.

In one embodiment, the organometallic complexes corresponding to Formula I and/or Formula II as disclosed herein are delivered to a substrate in pulses alternating with pulses of an oxygen source, such as a reactive oxygen species. Examples of such oxygen sources include, without limitation, $H_2O$, $H_2O_2$, $O_2$, ozone, air, i-PrOH, t-BuOH or $N_2O$.

In one embodiment, a molybdenum nitride (MoN, $Mo_2N$, or MoN/$Mo_2N$), and/or a molybdenum oxide ($MoO_2$, $MoO_3$, or $MoO_2$/$MoO_3$) film can be formed by delivering for deposition at least one complex according to Formula I and/or Formula II, independently or in combination with a co-reactant. In this regard, the co-reactant may be deposited or delivered to or passed over a substrate, independently or in combination with the at least one complex. Examples of such co-reactants include, but are not limited to hydrogen, hydrogen plasma, oxygen, air, water, $H_2O_2$, ammonia, a hydrazine, a borane, a silane, such as a trisilane, ozone or any combination thereof. Examples of suitable boranes include, without limitation, hydridic (i.e., reducing) boranes such as borane, diborane, triborane and the like. Examples of suitable silanes include, without limitation, hydridic silanes such as silane, disilane, trisilane, and the like. Examples of suitable hydrazines include, without limitation, hydrazine ($N_2H_4$) and/or a hydrazine optionally substituted with one or more alkyl groups (i.e., an alkyl-substituted hydrazine) such as methylhydrazine, tert-butylhydrazine, N,N- or N,N'-dimethylhydrazine, and the like.

In a particular embodiment, a co-reactant is used to form a $MoO_2$, $MoO_3$, or $MoO_2$/$MoO_3$ film by delivering for deposition at least one complex according to Formula I and/or Formula II, independently or in combination, with a co-reactant such as, but not limited to, air, $H_2O$, $O_2$, and/or ozone to a reaction chamber. A plurality of such co-reactants may be used.

In another particular embodiment, a co-reactant is used to form a MoN, $Mo_2N$, or MoN/$Mo_2N$ film by delivering for deposition at least one complex according to Formula I and/or Formula II, independently or in combination, with a co-reactant such as, but not limited to, ammonia, a hydrazine, or other nitrogen-containing compound (e.g., an amine) to a reaction chamber. A plurality of such co-reactants may be used.

In another particular embodiment, a co-reactant is used to form a molybdenum-containing metal film by delivering for deposition at least one complex according to Formula I and/or Formula II, independently or in combination, with a co-reactant such as, but not limited to, $H_2$, a hydrazine, a silane such as trisilane and/or ammonia to a reaction chamber.

In another embodiment, a mixed-metal film can be formed by a vapor deposition process which vaporizes a complex of Formula I and/or Formula II disclosed herein in combination, but not necessarily at the same time, with a co-complex having a metal different from molybdenum.

A variety of substrates can be used in the methods of the present invention. For example, the complexes according to Formula I and/or Formula II as disclosed herein may be delivered or passed over a variety of substrates such as, but not limited to, silicon such as Si(100), silicon oxide, silicon nitride, tantalum, tantalum nitride, copper, ruthenium, titanium nitride, tungsten, and tungsten nitride.

In a particular embodiment, the methods of the invention are utilized for applications such as dynamic random access memory (DRAM) and complementary metal oxide semiconductor (CMOS) for memory and logic applications, on substrates such as silicon chips.

Any of the molybdenum complexes described herein may be used to prepare thin films of molybdenum metal, molybdenum oxides, and/or molybdenum nitrides. Such films may find application as oxidation catalysts, anode materials (e.g., SOFC or LIB anodes), conducting layers, sensors, diffusion barriers/coatings, super- and non-superconducting materials/coatings, tribological coatings, and/or, protective coatings. It is understood by one of ordinary skill in the art that the film properties (e.g., conductivity) will depend on a number of factors, such as the metal(s) used for deposition, the presence or absence of co-reactants and/or co-complexes, the thickness of the film created, the parameters and substrate employed during growth and subsequent processing.

Fundamental differences exist between the thermally-driven CVD process and the reactivity-driven ALD process. The requirements for precursor properties to achieve optimum performance vary greatly. In CVD a clean thermal decomposition of the complex to deposit the required species onto the substrate is critical. However, in ALD such a thermal decomposition is to be avoided at all costs. In ALD, the reaction between the input reagents must be rapid at the surface resulting in formation of the target material on the substrate. However, in CVD, any such reaction between species is detrimental due to their gas phase mixing before reaching the substrate, which could lead to particle formation. In general it is accepted that good CVD precursors do not necessarily make good ALD precursors due to the relaxed thermal stability requirement for CVD precursors. In this invention, Formula I and II molybdenum complexes possess enough thermal stability and reactivity toward select co-reactants to function as ALD precursors, and they possess clean decomposition pathways at higher temperatures to form desired materials through CVD processes as well. Therefore, molybdenum complexes described by Formula I and II are useful as viable ALD and CVD precursors.

EXAMPLES

The following examples are merely illustrative, and do not limit this disclosure in any way.

Unless otherwise noted, all manipulations were performed under an inert atmosphere (e.g, purified nitrogen or argon) using techniques for handling air-sensitive materials commonly known in the art (e.g., "Schlenk techniques").

Example 1

Preparation of $CpMo(CO)_2(\eta^3$-2-methylallyl)

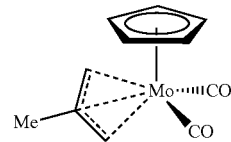

A 2 L round bottom flask equipped with magnetic stirrer was charged with $Mo(CO)_6$ (30 g, 0.114 mol) followed by acetonitrile (450 mL). The mixture was refluxed for 4 hours under nitrogen atmosphere (until no more $Mo(CO)_6$ sublimed out), giving a yellow colored solution. The solution was allowed to cool to room temperature (RT), and then 3-chloro-2-methylpropene (22.2 mL, 0.228 mol) was added slowly by syringe. During addition, an orange color was formed and CO evolution was observed. The mixture was stirred overnight at 50° C. and then allowed to settle. The resulting yellow precipitate was cannula filtered, then washed with acetonitrile (5 mL). After drying under reduced pressure, $Mo(CO)_2(MeCN)_2(\eta^3$-2-methylallyl)Cl was obtained as a yellow powder, yield 29 g (80%).

A solution of NaCp was prepared by drop-wise addition of freshly cracked cyclopentadiene (5.9 g, 0.089 mol) to a suspension of sodium hydride (2.1 g, 0.089 mol) in tetrahydrofuran (THF) (200 mL), then stirred at RT until $H_2$ evolution had ceased. The resulting solution was added to a solution of $Mo(CO)_2(MeCN)_2(\eta^3$-2-methylallyl)Cl (29 g, 0.089 mol) in THF (350 mL), slowly by cannula. The resulting dark-red solution was stirred overnight at RT, wherein a pale precipitate of NaCl formed. The solvent was removed under reduced pressure, and then the residue was extracted with hexane (2×0.5 L). The yellow/brown colored solution was filtered and then concentrated to approximately 100 mL, at which point a yellow solid had precipitated out. This solid was collected by filtration and dried under reduced pressure. A further batch of product was obtained by concentrating the solution down further and cooling in the freezer.

Yield of $CpMo(CO)_2(\eta^3$-2-methylallyl)=18 g (58% from $Mo(CO)_6$).

$^1$H NMR ($C_6D_6$): δ 1.53 (s, 2H, allyl-H), 1.66 (s, 3H, allyl-Me), 2.62 (s, 2H, allyl-H), 4.51 (s, 5H, Cp-H) ppm.

FIG. 1 shows a TGA plot of $CpMo(CO)_2(\eta^3$-2-methylallyl) with a temperature ramp from RT to 530° C.

Example 2

Preparation of $MeCpMo(CO)_2(\eta^3$-2-methylallyl)

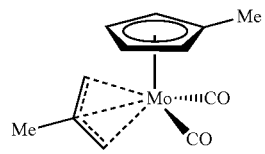

Mo(CO)$_2$(MeCN)$_2$($\eta^3$-2-methylallyl)Cl was prepared as described in Example 1 above. A solution of NaMeCp was prepared by drop-wise addition of freshly cracked methylcyclopentadiene (6.3 g, 0.079 mol) to a suspension of sodium hydride (1.9 g, 0.079 mol) in THF (300 mL), then stifling at RT until H$_2$ evolution had ceased. The resulting solution was added to a solution of Mo(CO)$_2$(MeCN)$_2$($\eta^3$-2-methylallyl)Cl (25 g, 0.077 mol) in THF (400 mL), slowly by cannula. The resulting dark-red solution was stirred overnight at RT, wherein a pale precipitate of NaCl formed. The mixture was cannula-filtered and the resulting clear solution evaporated, affording a dark-red liquid. The residue was extracted with hexane (300 mL). The reddish-brown solution was filtered and then the solvent was removed under reduced pressure. The red/brown liquid was distilled at 110-120° C. (0.5 Torr) in short-path distillation apparatus, affording MeCpMo(CO)$_2$($\eta^3$-2-methylallyl) as an orange liquid/low-melting solid, 15 g (68%).

$^1$H NMR (C$_6$D$_6$): δ 1.30 (s, 2H, allyl-H), 1.49 (s, 3H, Cp-Me), 1.70 (s, 3H, allyl-Me), 2.78 (s, 2H, allyl-H), 4.49 (m, 2H, Cp-H), 4.57 (m, 2H, Cp-H) ppm.

Figure 2:
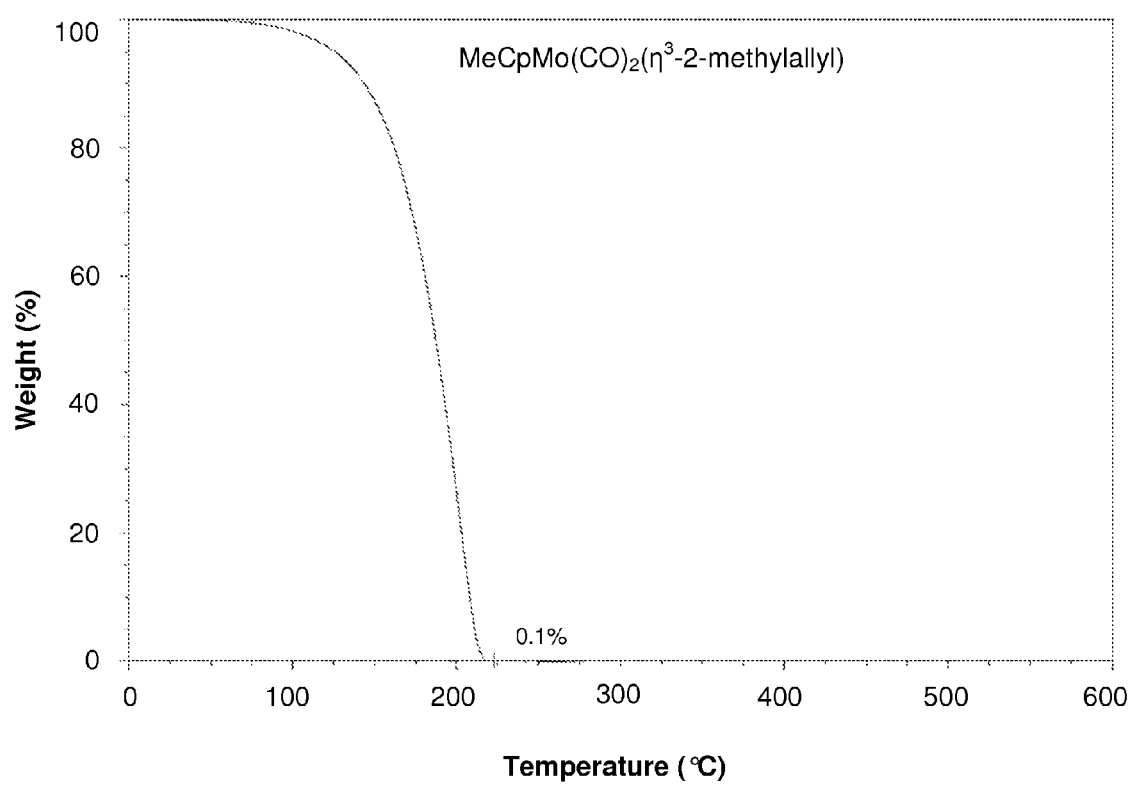
FIG. 2 is a graphical representation of TGA data demonstrating % weight loss vs. temperature of MeCpMo(CO)$_2$($\eta^3$-2-methylallyl).

FIG. 2 shows a TGA plot of MeCpMo(CO)$_2$($\eta^3$-2-methylallyl) with a temperature ramp from RT to 275° C. The TGA plots of CpMo(CO)$_2$($\eta^3$-2-methylallyl) and MeCpMo(CO)$_2$($\eta^3$-2-methylallyl) were similar and each show a one-step weight loss between the temperatures of ~125° C. and ~215° C., with a final percent residue of ~0.2%.

Example 3

Preparation of i-PrCpMo(CO)$_2$($\eta^3$-2-methylallyl)

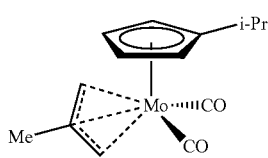

Mo(CO)$_2$(MeCN)$_2$($\eta^3$-2-methylallyl)Cl was prepared as described in Example 1 above. A solution of Na(i-Pr)Cp (sodium isopropylcyclopentadienide, 22 g, 0.169 mol) in THF (150 mL) was added to a solution of Mo(CO)$_2$(MeCN)$_2$($\eta^3$-2-methylallyl)Cl (54.4 g, 0.168 mol) in THF (500 mL), slowly by cannula. The resulting dark-red solution was stirred overnight at RT, wherein a pale precipitate of NaCl formed. The solvent was removed under reduced pressure. The resulting dark-red/brown oily residue was extracted with hexane (300 mL) and the combined extracts filtered by cannula. The solvent was removed under reduced pressure and the resulting red liquid was distilled at 110-130° C. (0.5 Torr), affording i-PrCpMo(CO)$_2$($\eta^3$-2-methylallyl) as a red liquid, 27 g (43% from Mo(CO)$_6$).

$^1$H NMR (C$_6$D$_6$): δ 0.90 (d, 6H, CHMe$_2$), 1.51 (s, 2H, allyl-H), 1.69 (s, 3H, allyl-Me), 2.18 (sept, 1H, CHMe$_2$), 2.69 (s, 2H, allyl-H), 4.47 (m, 2H, Cp-H), 4.59 (m, 2H, Cp-H) ppm.

Figure 3:
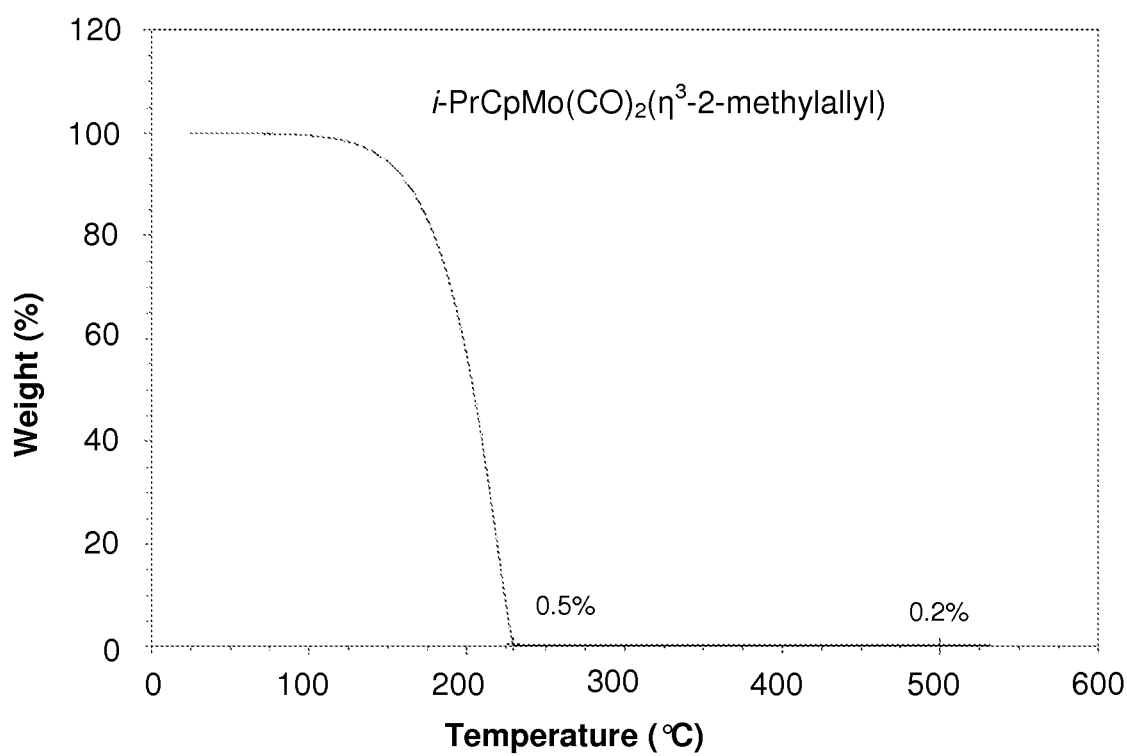
FIG. 3 is a graphical representation of TGA data demonstrating % weight loss vs. temperature of i-PrCpMo(CO)$_2$($\eta^3$-2-methylallyl).

FIG. 3 shows a TGA plot of i-PrCpMo(CO)$_2$($\eta^3$-2-methylallyl) with a temperature ramp from RT to 530° C.

Example 4

Preparation of MeCpMo(CO)$_2$($\eta^3$-2-tert-butylallyl)

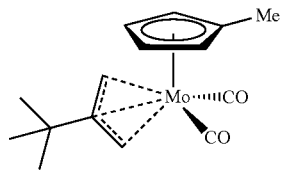

A 1 L round bottom flask equipped with magnetic stirrer was charged with Mo(CO)$_6$ (11 g, 0.042 mol) followed by acetonitrile (300 mL). The mixture was refluxed for 8 hours under nitrogen atmosphere, giving a yellow colored solution. The solution was allowed to cool to RT, and then 2-bromomethyl-3,3-dimethyl-1-butene (8 g, 0.045 mol) was added slowly by syringe. During addition, a red solution was formed and CO evolution was observed. The mixture was stirred for 48 hours at 60° C. The resulting solution was cooled to 30° C. and then the solvent was removed under reduced pressure, affording Mo(CO)$_2$(MeCN)$_2$($\eta^3$-2-tert-butylallyl)Br as an orange solid, yield 16.2 g (94%).

A solution of NaMeCp was prepared by drop-wise addition of freshly cracked methylcyclopentadiene (3.2 g, 0.04 mol) to a suspension of sodium hydride (1 g, 0.041 mmol) in THF (100 mL), then stirring at 20° C. until H$_2$ evolution had ceased. The resulting solution was slowly added to a solution of Mo(CO)$_2$(MeCN)$_2$($\eta^3$-2-tert-butylallyl)Br (16.2 g, 0.039 mol) in THF (200 mL). The resulting dark-red solution was stirred overnight at 20° C., wherein a pale precipitate of NaBr formed. The solvent was removed under reduced pressure. The resulting dark-red/brown oily residue was extracted with hexane (200 mL) and the combined extracts filtered by cannula. The solvent was removed under reduced pressure and the resulting red oil was distilled at 120-130° C. (0.4 Torr), affording MeCpMo(CO)$_2$($\eta^3$-2-tert-butylallyl) as a low-melting orange solid, 10 g (73% from Mo(CO)$_6$).

$^1$H NMR (C$_6$D$_6$): $^1$H NMR (C$_6$D$_6$): δ 1.10 (s, 9H, t-Bu), 1.12 (s, 2H, allyl-H), 1.41 (s, 3H, Cp-Me), 2.91 (s, 2H, allyl-H), 4.44 (m, 2H, Cp-H), 4.55 (m, 2H, Cp-H) ppm.

Figure 4:
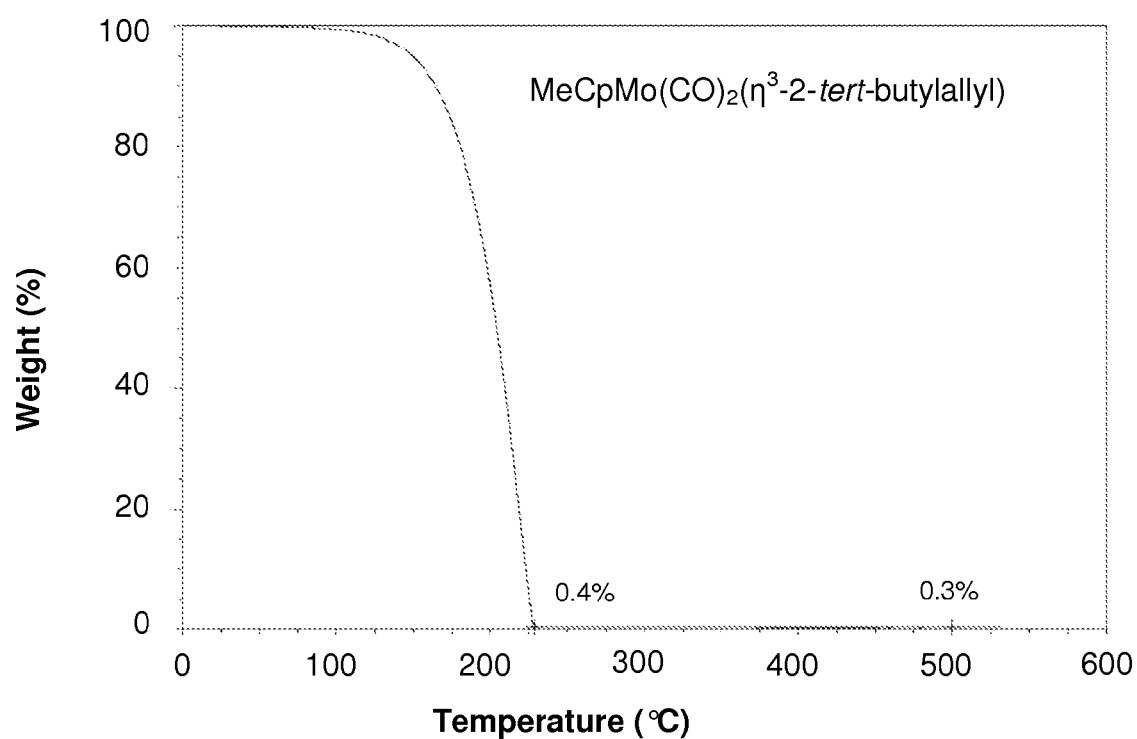
FIG. 4 is a graphical representation of TGA data demonstrating % weight loss vs. temperature of MeCpMo(CO)$_2$($\eta^3$-2-tert-butylallyl).

FIG. 4 shows a TGA plot of MeCpMo(CO)$_2$($\eta^3$-2-tert-butylallyl) with a temperature ramp from RT to 530° C. The TGA plots of i-PrCpMo(CO)$_2$(2-Me-allyl) and MeCpMo(CO)$_2$($\eta^3$-2-tert-butylallyl) were similar and show a one-step weight loss between the temperatures of ~150° C. and ~230° C., with a final percent residue of ~0.4%.

Physical properties of the organometallic complexes prepared in Examples 1-4 are summarized in Table 2.

TABLE 2

| Complex | Form | MP (° C.) | BP (° C.) | Vapor Pressure Equation |
|---|---|---|---|---|
| CpMo(CO)$_2$($\eta^3$-2-methylallyl) | Solid | 78 | 110-120 (0.5 Torr) | $\log_{10}P = 11.85 - 3350/T$ |
| MeCpMo(CO)$_2$($\eta^3$-2-methylallyl) | Low-melting solid | 30 | 110-120 (0.5 Torr) | $\log_{10}P = 10.522 - 2710/T$ |

TABLE 2-continued

| Complex | Form | MP (° C.) | BP (° C.) | Vapor Pressure Equation |
|---|---|---|---|---|
| i-PrCpMo(CO)$_2$($\eta^3$-2-methylallyl) | Liquid | — | 110-130 (0.5 Torr) | $\log_{10}P =$ 10.722 − 2905/T |
| MeCpMo(CO)$_2$($\eta^3$-2-tert-butylallyl) | Low-melting solid | 30 | 120-130 (0.5 Torr) | — |

Example 5

Preparation of ($\eta^6$-Et$_x$C$_6$H$_{6-x}$)Mo($\eta^3$-allyl)$_2$ (where x=0-4)

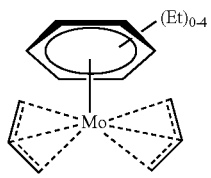

It is noted that the starting material, Mo($\eta^6$-Et$_x$C$_6$H$_{6-x}$)$_2$, is a mixture of several complexes where x is zero to 4 with varying occurrences of ethyl groups substituted on the coordinated arene. In a glovebag, Mo($\eta^6$-Et$_x$C$_6$H$_{6-x}$)$_2$ (10.0 g) was loaded into a 1 L Schlenk flask. The flask was equipped with a magnetic stirbar, sealed with a rubber septum and removed from the glovebag. The flask was then pump/purged with vacuum/N$_2$ three times before being placed under a dynamic N$_2$ atmosphere. The flask was charged with 250 mL of anhydrous toluene via cannula and the dark-green mixture was magnetically stirred. Allyl chloride (4.0 mL, 49 mmol) was slowly added to the stirring Mo(Et$_x$C$_6$H$_{6-x}$)$_2$/toluene mixture and the resulting reaction mixture was stirred overnight. The volatiles were removed from the resulting dark-purple solution under reduced pressure giving a dark-purple oil. The dark-purple oil, assumed to be [($\eta^6$-Et$_x$C$_6$H$_{6-x}$)($\eta^3$-allyl)Mo(μ-Cl)]$_2$, was extracted with 2×250 mL absolute ethanol and filtered using a cannula filter. The purple filtrates were combined and the volatiles were removed under reduced pressure. The mixture was slurried in 500 mL anhydrous hexane and the volatiles again removed under reduced pressure. The dark-purple oil was dissolved in 500 mL of anhydrous THF and the mixture was magnetically stirred. Allylmagnesium chloride (2.0 M in THF, 18.0 mL, 36.0 mmol) was slowly added to the reaction mixture via syringe. The mixture was stirred overnight. The brown reaction mixture was then cooled to −30° C. and excess allylmagnesium chloride was quenched with a few drops of water added via syringe. The brown suspension was filtered via cannula filtration and the volatiles were removed from the filtrate under reduced pressure. The mixture was slurried in 500 mL anhydrous hexane and the volatiles removed under reduced pressure (to ensure complete removal of THF). The product was then extracted with 2×500 mL of anhydrous hexane and filtered via cannula filtration. The filtrates were combined and the volatiles removed under reduced pressure giving 4.0 g of a dark-purple oil. The dark-purple oil was distilled at 130-140° C. and 0.5 Torr to give 0.3 g (3%) of the desired product as a yellow-orange oil.

The desired product is a mixture of species and exhibits a complex $^1$H NMR. $^1$H NMR (C$_6$D$_6$): δ 0.7-1.8 (m, ethyl and 1-allyl-H), 2.4-2.6 (m, 1-allyl-H), 3.7-4.1 (m, 2-allyl-H), 6.8-7.2 (m, aryl-H) ppm.

Example 6

Deposition Experiments with CpMo(CO)$_2$($\eta^3$-2-methylallyl)

Figure 5:
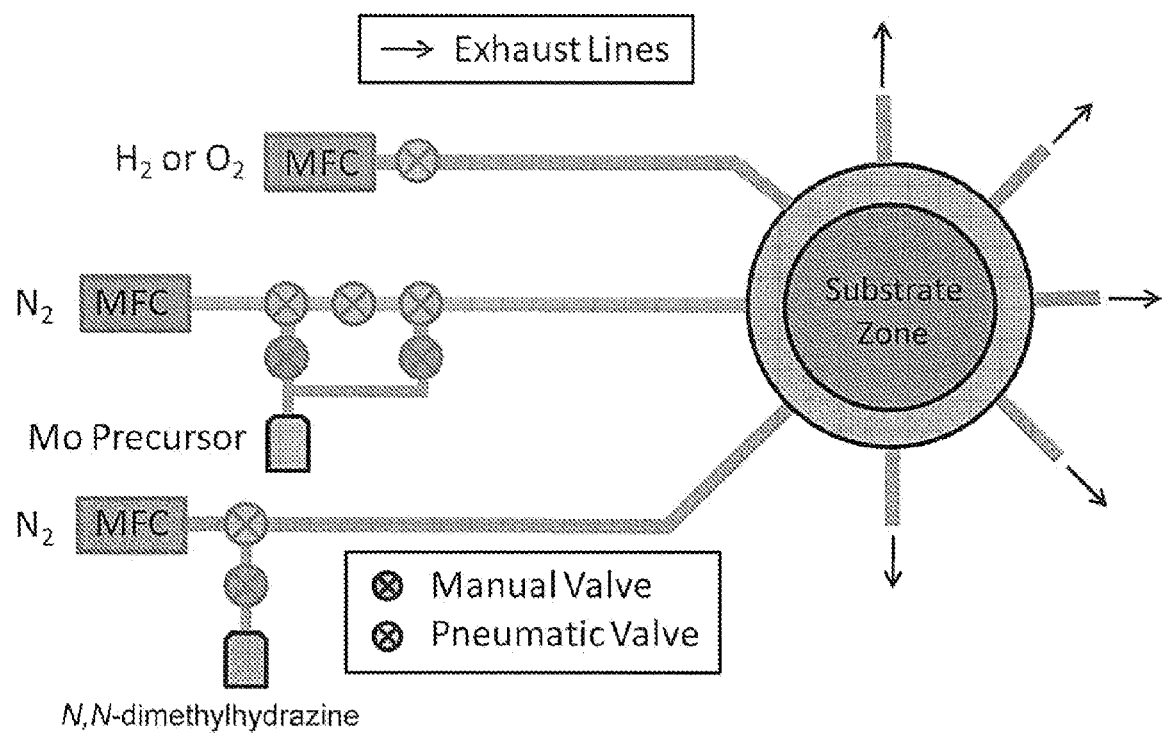
FIG. 5 is a schematic of a reactor used for CVD and ALD, according to some embodiments. Where indicated, "MFC" refers to a mass flow controller.

In all deposition experiments in this example, cyclopentadienyl molybdenum dicarbonyl 2-methylallyl (CpMo(CO)$_2$($\eta^3$-2-methylallyl)) was used as the molybdenum source. FIG. 5 is a schematic of a reactor used for CVD and ALD experiments in this example. The Mo source was kept at 90° C. with a nitrogen carrier gas flow of 80 sccms and was pulsed for 1.0 s during experiments. The co-reactants used were oxygen, N,N-dimethylhydrazine, and hydrogen gas. In all the examples, the baseline reactor pressure was between 1.2 and 1.5 Torr. The substrates used were silicon dioxide (100 Å on silicon), silicon (100) p-doped, and tantalum nitride. Deposition occurred on all substrates in the examples described below. XPS spectra and cross sectional SEM micrographs for films deposited on Si were analyzed. As a measure of uniformity, film thicknesses were measured by cross-sectional SEM at many different points on the substrate.

Example 6A

Deposition of Mo by Pulsed Chemical Vapor Deposition—No Co-Reactant

A Mo-containing film was deposited by chemical vapor deposition with the following parameters:
Substrate temperature: 350° C.
Co-reactant: none
Nitrogen Purge Time: 5.0 s
Pulse Train: 1.0 s Mo precursor/5.0 s nitrogen purge
Total cycles: 1000

Figure 6:
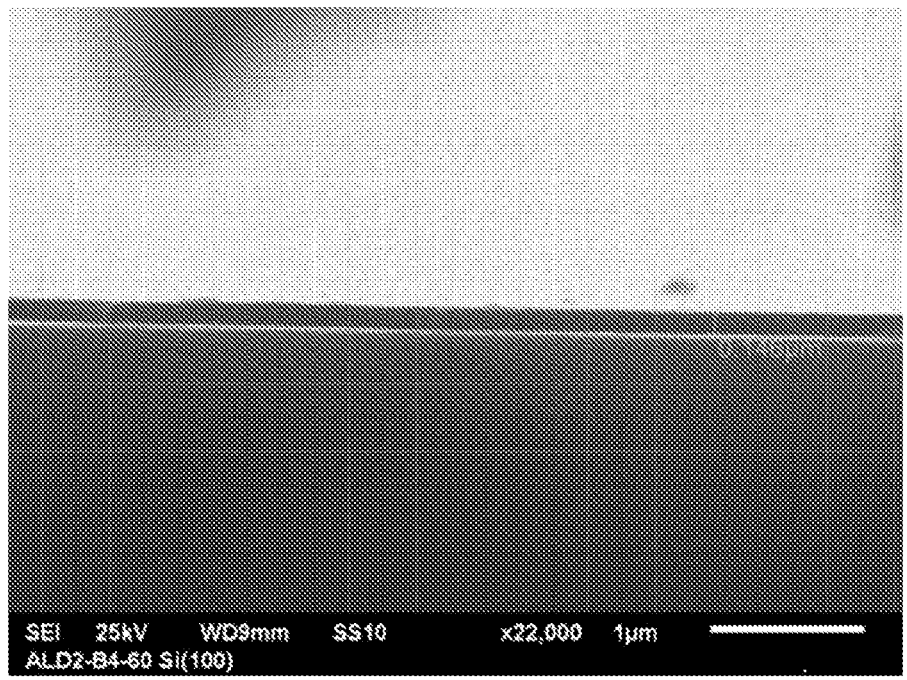
FIG. 6A is a scanning electron microscopy (SEM) micrograph of a Mo-containing film deposited on hydrogen terminated Si(100) by CVD at 350° C.
FIG. 6B is a SEM micrograph of a Mo-containing film deposited on hydrogen terminated Si(100) by CVD at 350° C.
Figure 6:
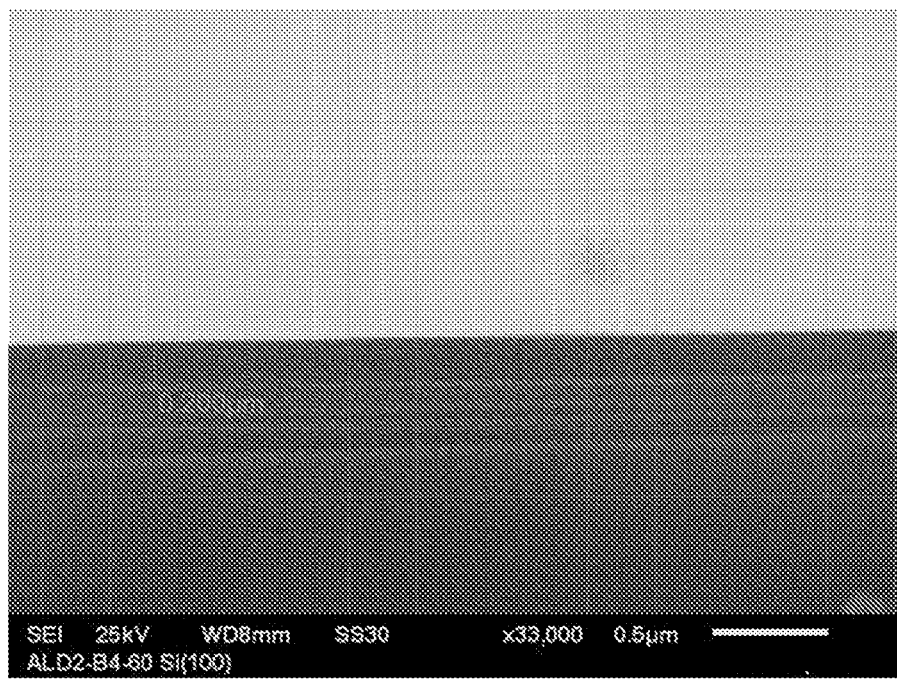

FIGS. 6A and 6B are selected cross-sectional SEM micrographs of the film deposited on hydrogen terminated Si(100) using the above parameters. The film thicknesses varied from 146-250 nm across the substrate.

Figure 7:
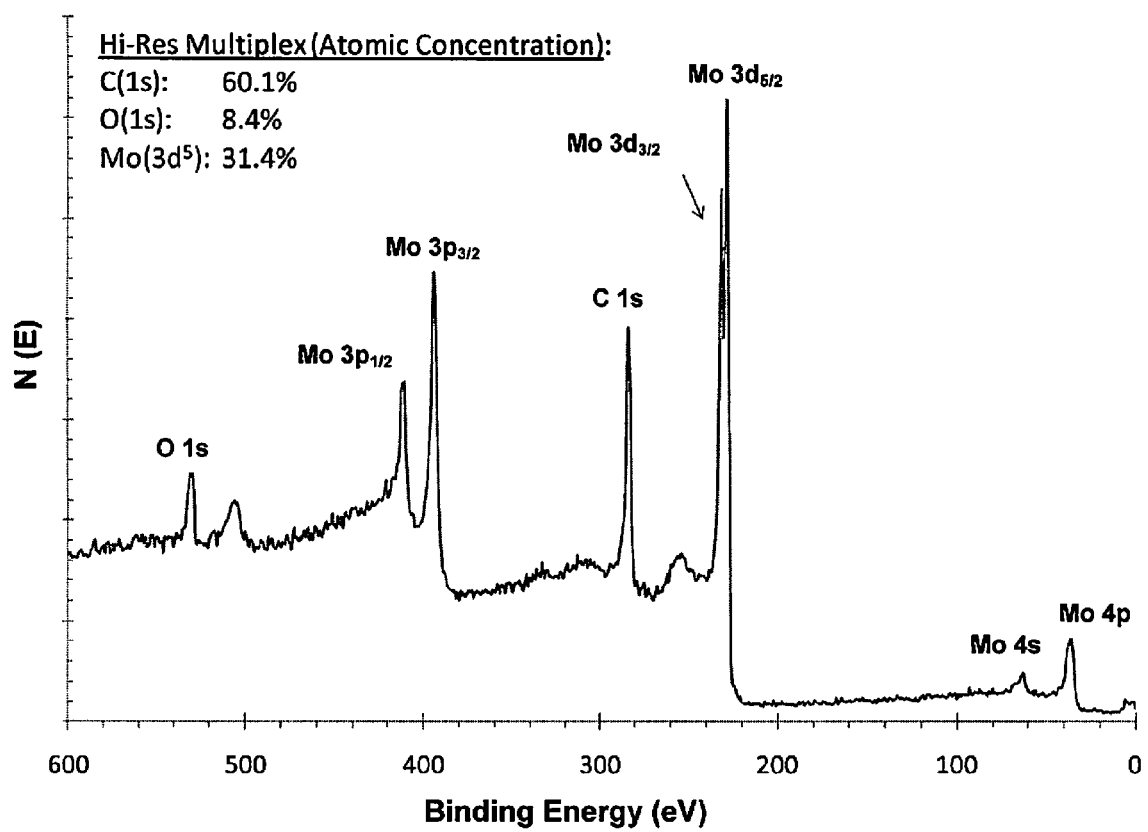
FIG. 7 is a graphical representation of X-ray photoelectron spectroscopy (XPS) data of a film deposited by CVD at 350° C. on hydrogen terminated Si(100) after sputtering with argon ions for two minutes.

FIG. 7 is XPS spectra and compositional analysis of the film deposited on hydrogen terminated Si(100) after sputtering with argon ions for two minutes.

Example 6B

Deposition of Mo by Pulsed Chemical Vapor Deposition with Hydrogen as a Co-Reactant A Mo-containing film was deposited by chemical vapor deposition with the following parameters:
Substrate temperature: 350° C.
Co-reactant: hydrogen gas (50 sccms), co-flowed with Mo precursor. Hydrogen gas was constantly flowed throughout the deposition run.
Nitrogen Purge Time: 5.0 s
Pulse Train: 1.0 s Mo precursor/5.0 s nitrogen purge
Total cycles: 1000

Figure 8:
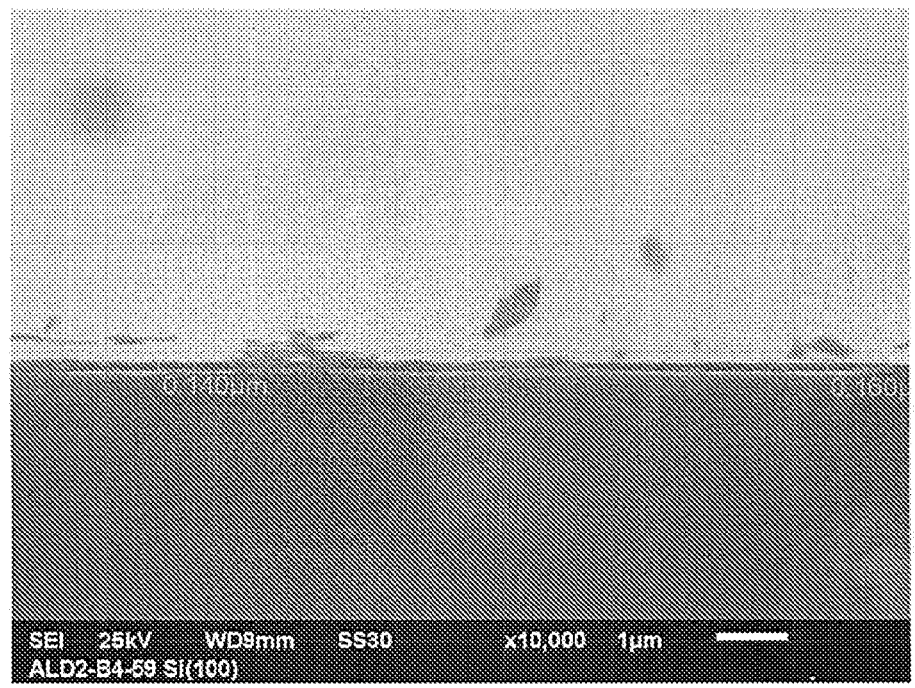
FIG. 8A is a SEM micrograph of a Mo-containing film deposited on hydrogen terminated Si(100) by CVD at 350° C. with hydrogen as a co-reactant.
FIG. 8B is a SEM micrograph of a Mo-containing film deposited on hydrogen terminated Si(100) by CVD at 350° C. with hydrogen as a co-reactant.
Figure 8:
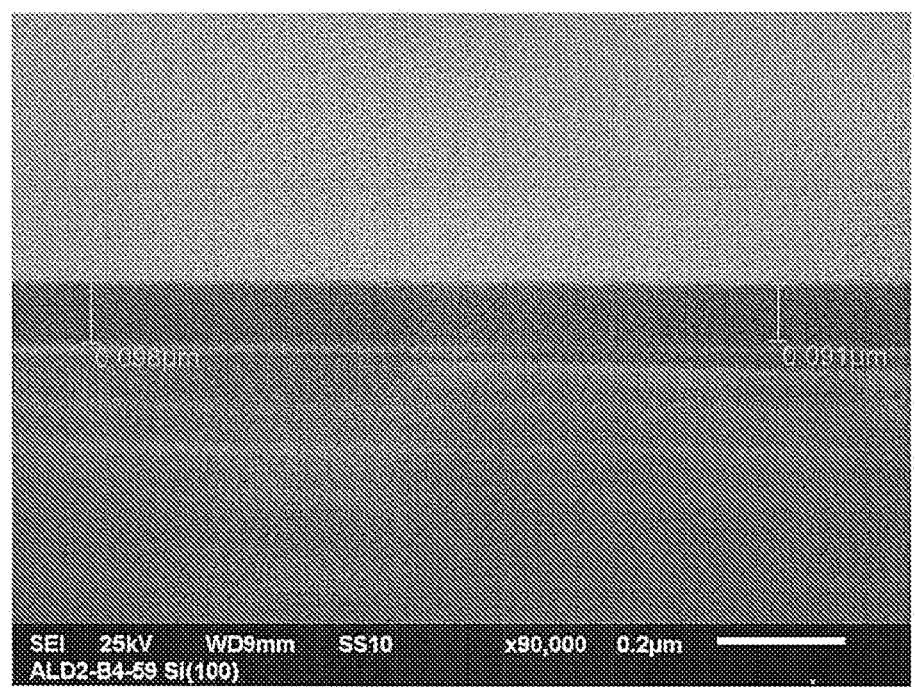

FIGS. 8A and 8B are selected cross-sectional SEM micrographs of the film deposited on hydrogen terminated Si(100) using the above parameters. The film thicknesses varied from 91-160 nm across the substrate.

Figure 9:
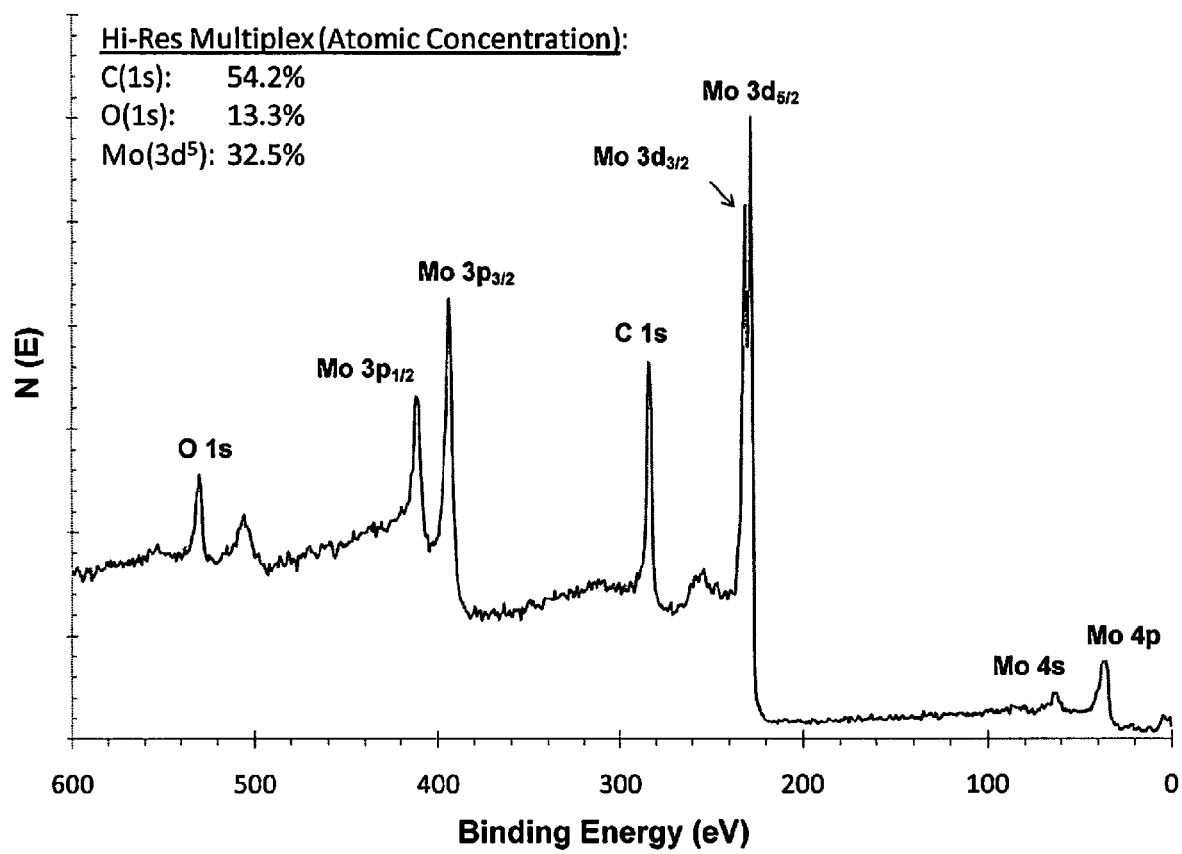
FIG. 9 is a graphical representation of XPS data of a Mo-containing film deposited by CVD at 350° C. with hydrogen as a co-reactant on hydrogen terminated Si(100) after sputtering with argon ions for two minutes.

FIG. 9 is XPS spectra and compositional analysis of the film deposited on hydrogen terminated Si(100) after sputtering with argon ions for two minutes.

Example 6C

Deposition of Mo by Pulsed Chemical Vapor Deposition with Hydrazine as a Co-Reactant A Mo-containing film was deposited by chemical vapor deposition with the following parameters:
Substrate temperature: 350° C.
Co-reactant: hydrazine (23° C.) with a nitrogen carrier gas flow of 60 sccms, co-flowed with Mo precursor.
Nitrogen Purge Time: 5.0 s
Pulse Train: 3.0 s Mo precursor and 1.0 s hydrazine/5.0 s nitrogen purge
Total cycles: 2000

Figure 10:
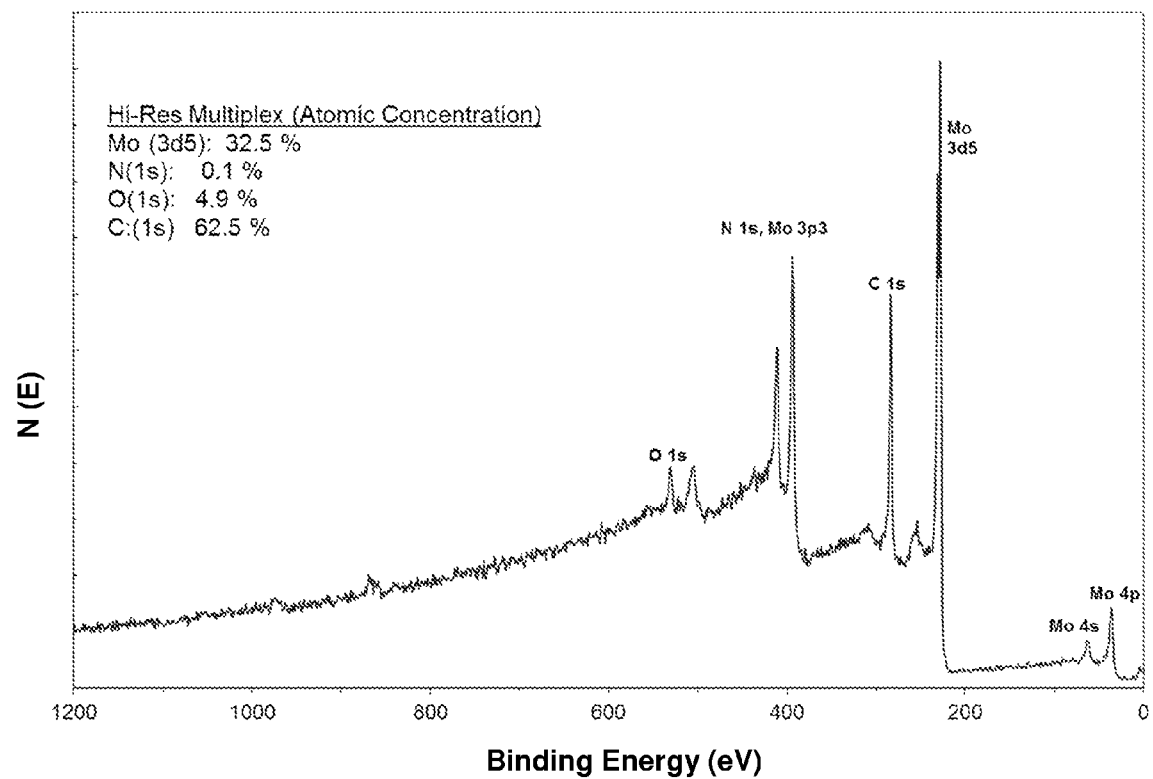
FIG. 10 is a graphical representation of XPS data of a Mo-containing film deposited by CVD at 350° C. with hydrazine as a co-reactant on hydrogen terminated Si(100) after sputtering with argon ions for two minutes.

FIG. 10 is XPS spectra and compositional analysis of the film deposited on hydrogen terminated Si(100) under the above parameters. The film was sputtered with argon ions to remove surface contaminants.

Figure 11:
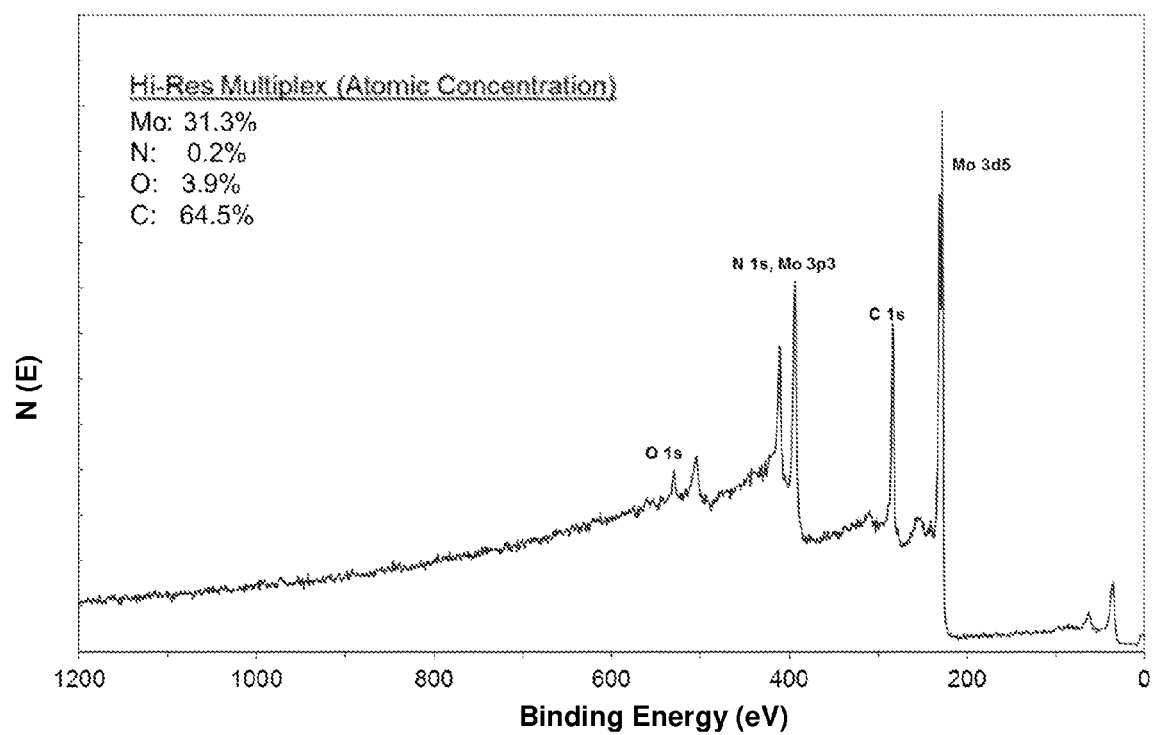
FIG. 11 is a graphical representation of XPS data of a Mo-containing film deposited by CVD at 350° C. with hydrazine as a co-reactant on tantalum nitride after sputtering with argon ions for two minutes.

FIG. 11 is XPS spectra and compositional analysis of the film deposited on tantalum nitride under the above parameters. The film was sputtered with argon ions to remove surface contaminants.

Example 6D

Deposition of Mo by Pulsed Chemical Vapor Deposition with Ammonia as a Co-Reactant A Mo-containing film was deposited by chemical vapor deposition with the following parameters:
Substrate temperature: 350° C.
Co-reactant: ammonia gas (100 sccms), co-flowed with Mo precursor. Ammonia gas was flowed constantly throughout the deposition run.
Nitrogen Purge Time: 5.0 s
Pulse Train: 3.0 s Mo precursor/5.0 s nitrogen purge
Total cycles: 2000

Figure 12:
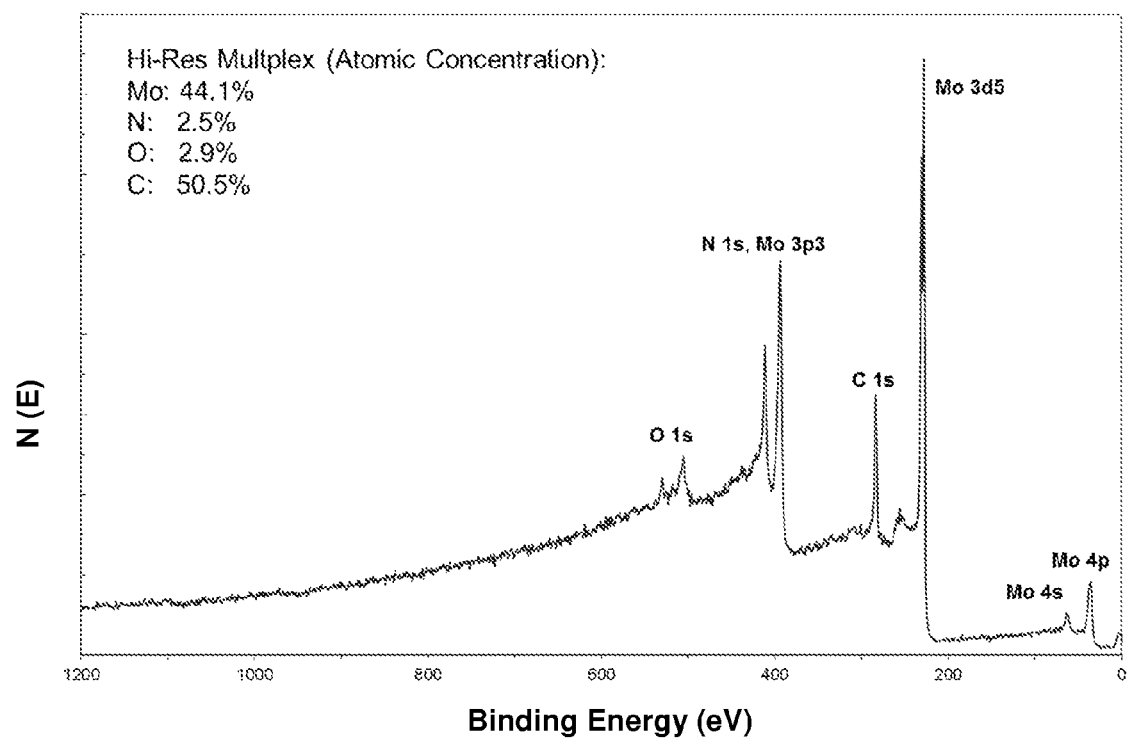
FIG. 12 is a graphical representation of XPS data of a Mo-containing film deposited by CVD at 350° C. with ammonia as a co-reactant on hydrogen terminated Si(100) after sputtering with argon ions for two minutes.

FIG. 12 is XPS spectra and compositional analysis of the film deposited on hydrogen terminated Si(100) under the above parameters. The film was sputtered with argon ions to remove surface contaminants.

Figure 13:
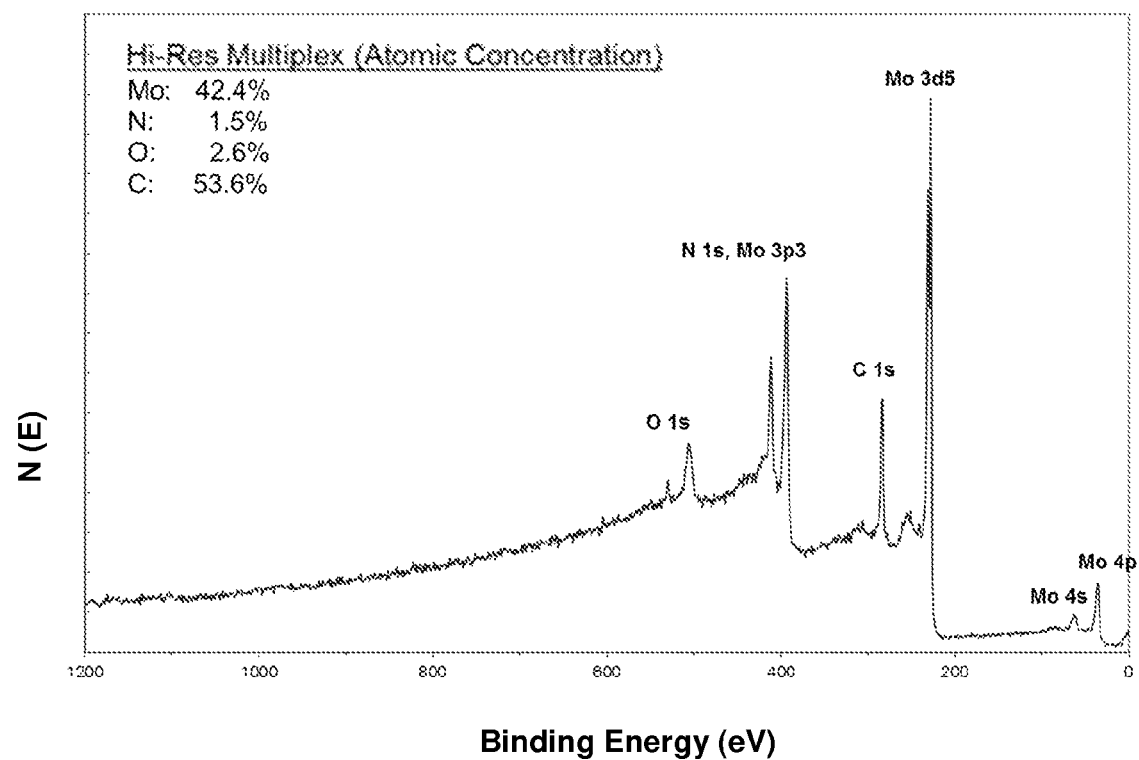
FIG. 13 is a graphical representation of XPS data of a Mo-containing film deposited by CVD at 350° C. with ammonia as a co-reactant on tantalum nitride after sputtering with argon ions for two minutes.

FIG. 13 is XPS spectra and compositional analysis of the film deposited on tantalum nitride under the above parameters. The film was sputtered with argon ions to remove surface contaminants.

Example 6E

Deposition of Mo by Atomic Layer Deposition with N,N-Dimethylhydrazine as a Co-Reactant A Mo-containing film was deposited by atomic layer deposition with the following parameters:
Substrate temperature: 250° C.
Co-reactant: N,N-dimethylhydrazine (15° C.) with a nitrogen carrier gas flow of 60 sccms
Nitrogen Purge Time: 5.0 s
Pulse Train: 1.0 s Mo precursor/5.0 s nitrogen purge/0.8 s N,N-dimethylhydrazine/5.0 s nitrogen purge
Total cycles: 2000

Figure 14:
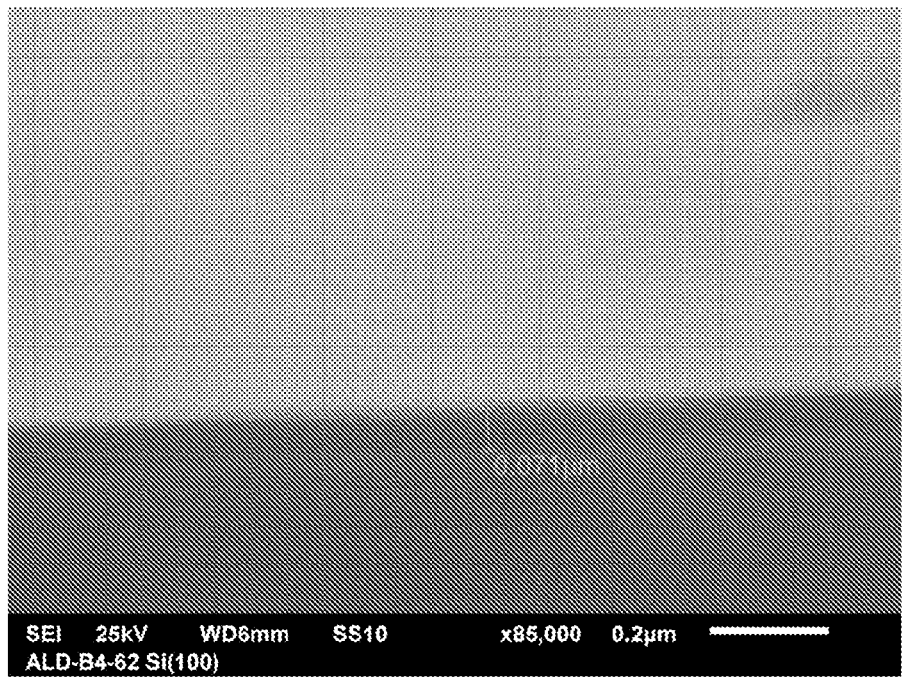
FIG. 14A is a SEM micrograph of a Mo-containing film deposited on hydrogen terminated Si(100) by ALD at 250° C. with N,N-dimethylhydrazine as a co-reactant.
FIG. 14B is a SEM micrograph of a Mo-containing film deposited on hydrogen terminated Si(100) by ALD at 250° C. with N,N-dimethylhydrazine as a co-reactant.
Figure 14:
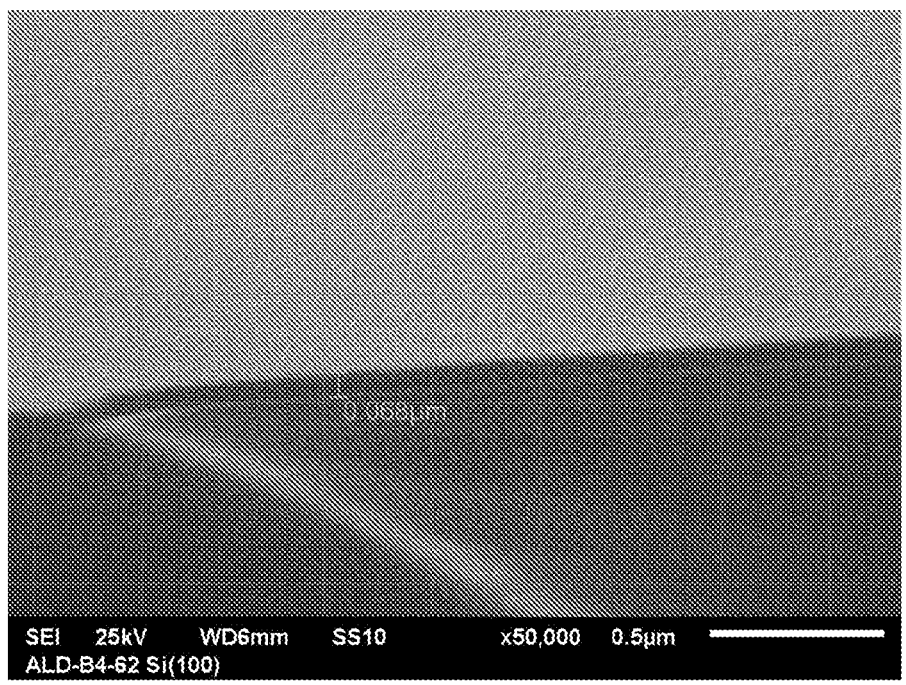

FIGS. 14A and 14B are selected cross-sectional SEM micrographs of the film deposited on hydrogen terminated Si(100) using the above parameters. The film thicknesses varied from 68-72 nm across the substrate.

Figure 15:
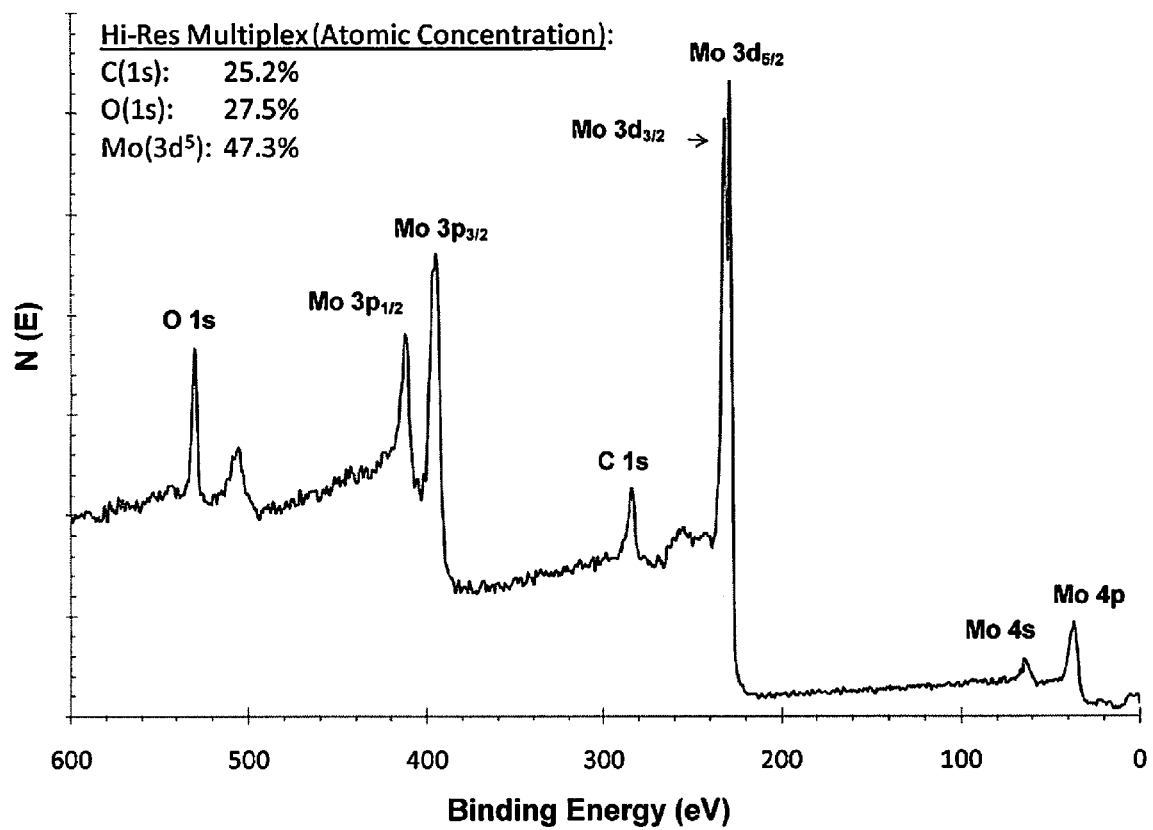
FIG. 15 is a graphical representation of XPS data of a Mo-containing film deposited by ALD at 250° C. with N,N-dimethylhydrazine as a co-reactant on hydrogen terminated Si(100) after sputtering with argon ions for two minutes.

FIG. 15 is XPS spectra and compositional analysis of the film deposited on hydrogen terminated Si(100) after sputtering with argon ions for two minutes.

Figure 16:
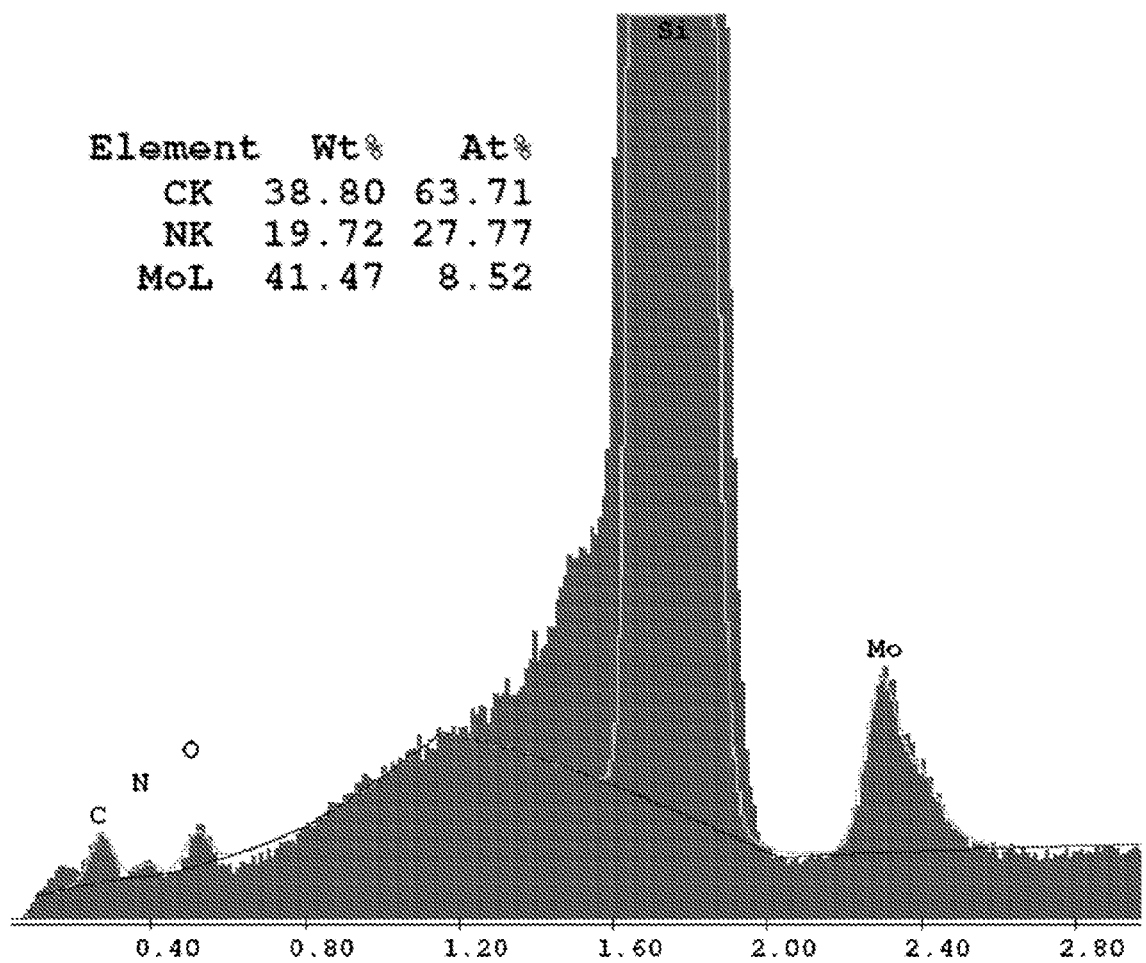
FIG. 16 is EDAX (energy dispersive X-ray spectroscopy) and compositional analysis of a Mo-containing film deposited by ALD at 250° C. with N,N-dimethylhydrazine as a co-reactant on hydrogen terminated Si(100).

FIG. 16 is EDAX and compositional analysis of the film deposited on hydrogen terminated Si(100) using the above parameters.

Example 6F

Deposition of Mo by Atomic Layer Deposition with Oxygen as a Co-Reactant

A molybdenum oxide-containing film was deposited by atomic layer deposition with the following parameters:
Substrate temperature: 250° C.
Co-reactant: oxygen 10 sccms
Nitrogen Purge Time: 5.0 s
Pulse Train: 1.0 s Mo precursor/5.0 s nitrogen purge/1.0 s oxygen/5.0 s nitrogen purge
Total cycles: 2000

Figure 17:
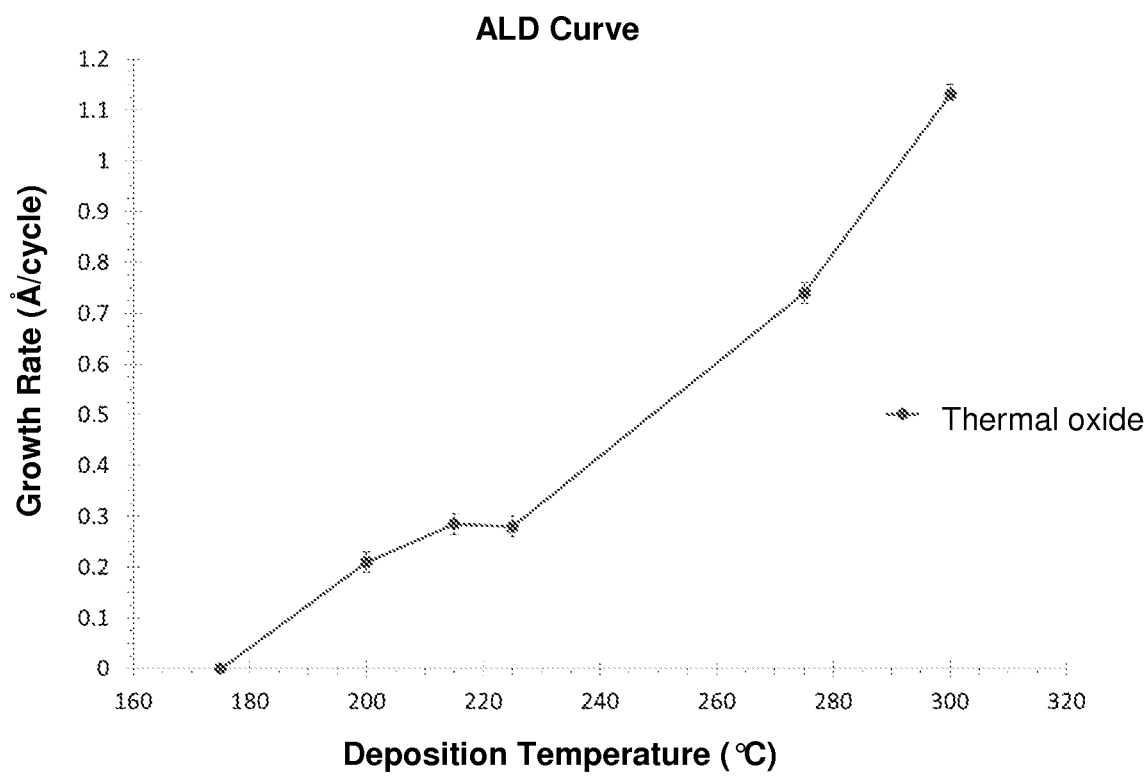
FIG. 17 is a graphical representation of Mo ALD curve data demonstrating growth rate vs. deposition temperature, for a Mo-containing film deposited on SiO$_2$ 1 K (100 nm of SiO$_2$ on Si), using oxygen as a co-reactant. The molybdenum precursor and oxygen pulse lengths were kept constant at 1.0 s.

As shown in FIG. 17, when oxygen was used as the co-reactant and $SiO_2$ 1 K was used as a substrate, an ALD window was observed to be between ~210° C. and ~225° C., with a constant growth rate of ~0.26 Å/cycle.

Figure 18:
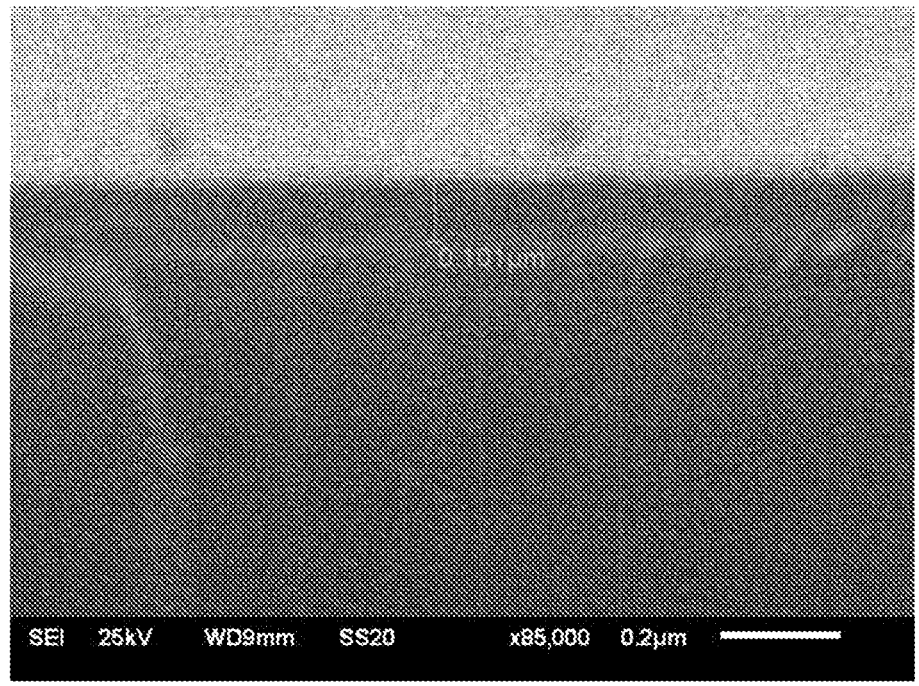
FIG. 18A is a SEM micrograph of a Mo-containing film deposited on hydrogen terminated Si(100) by ALD at 250° C. with oxygen as a co-reactant.
FIG. 18B is a SEM micrograph of a Mo-containing film deposited on hydrogen terminated Si(100) by ALD at 250° C. with oxygen as a co-reactant.
Figure 18:
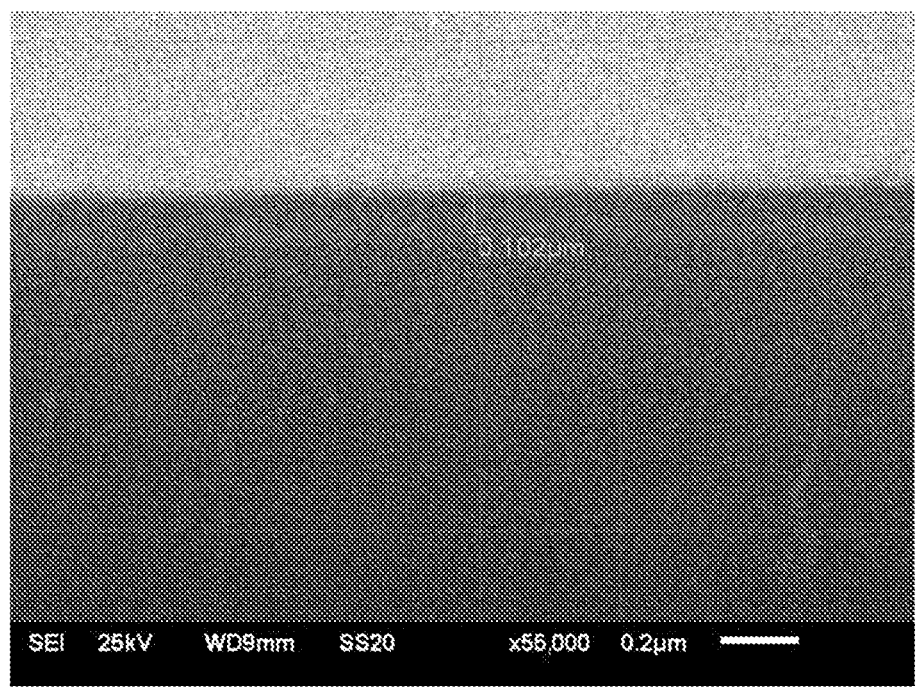

FIGS. 18A and 18B are selected cross-sectional SEM micrographs of the film deposited on hydrogen terminated Si(100) using the above parameters. The film thicknesses varied from 101-103 nm across the substrate.

Figure 19:
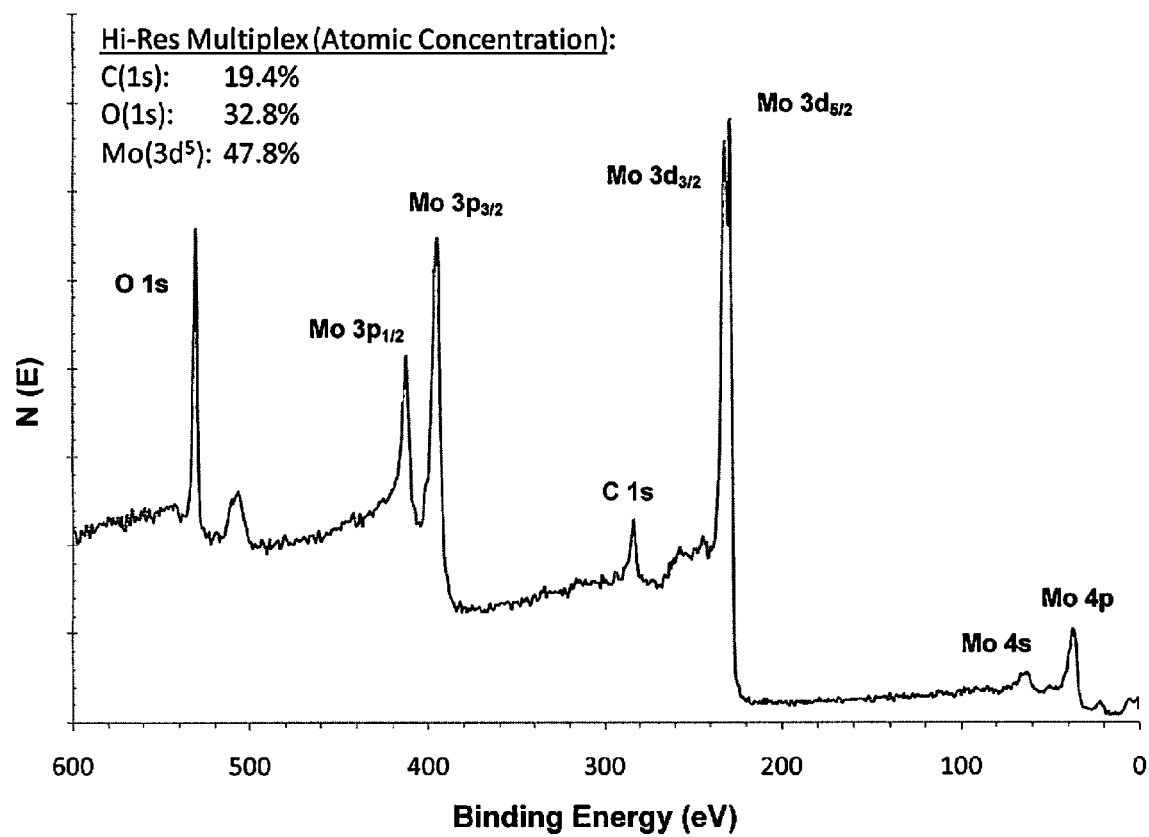
FIG. 19 is a graphical representation of XPS data of a Mo-containing film deposited by ALD at 250° C. with oxygen as a co-reactant on hydrogen terminated Si(100) after sputtering with argon ions for two minutes.

FIG. 19 is XPS spectra and compositional analysis of the film deposited on hydrogen terminated Si(100) after sputtering with argon ions for two minutes.

Figure 20:
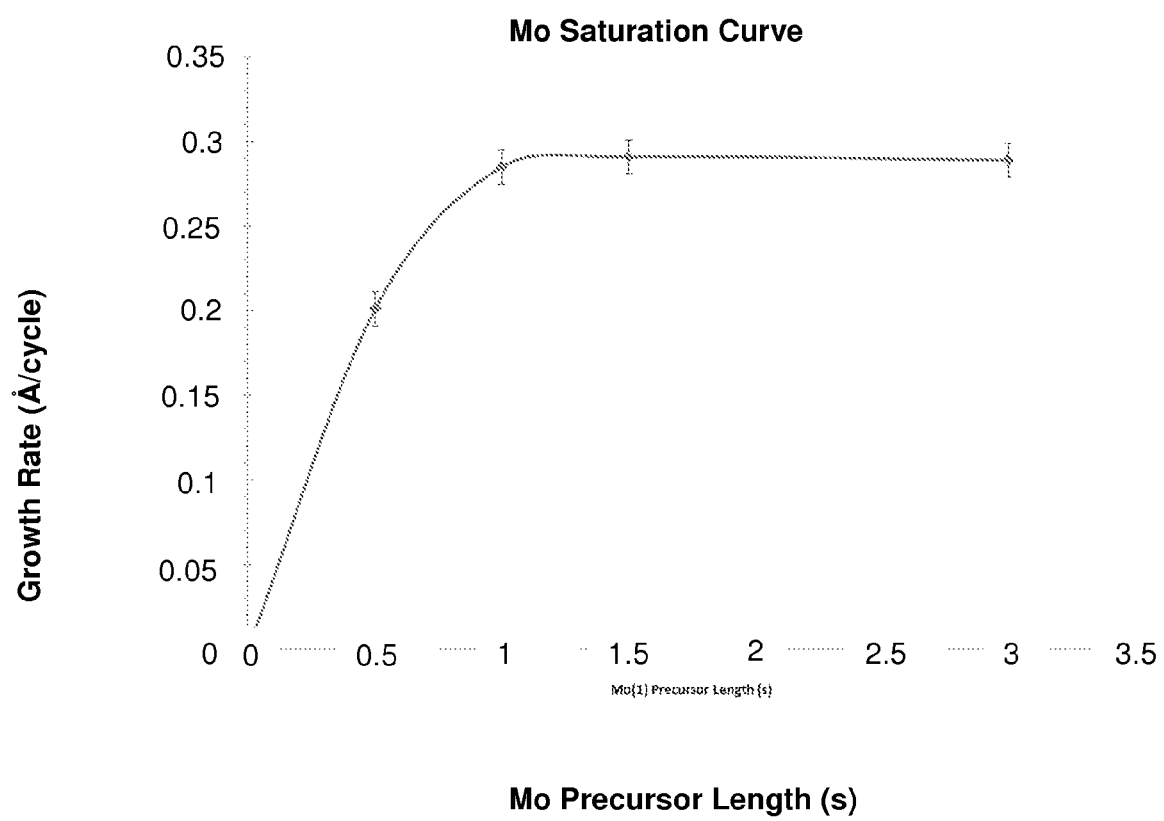
FIG. 20 is a graphical representation of Mo surface saturation data demonstrating growth rate vs. Mo precursor pulse length, using oxygen as co-reactant on SiO$_2$ 1 K.

In further growth studies using oxygen as a co-reactant (1.0 s pulse length), a plot of growth rate versus $CpMo(CO)_2(\eta^3$-2-methylallyl) precursor pulse length at a substrate (deposition) temperature of 215° C. was generated. As shown in FIG. 20, self-limiting film growth behavior occurs at Mo pulse lengths of ≥1.0 s.

Example 6G

Deposition of Mo by Atomic Layer Deposition with Water as a Co-Reactant

A Mo-containing film was deposited by atomic layer deposition with the following parameters:
Substrate temperature: 225° C.
Co-reactant: water
Nitrogen Purge Time: 5.0 s
Pulse Train: 2.0 s Mo complex/5.0 s $N_2$ purge/1.0 s
Total cycles: 2000

Figure 21:
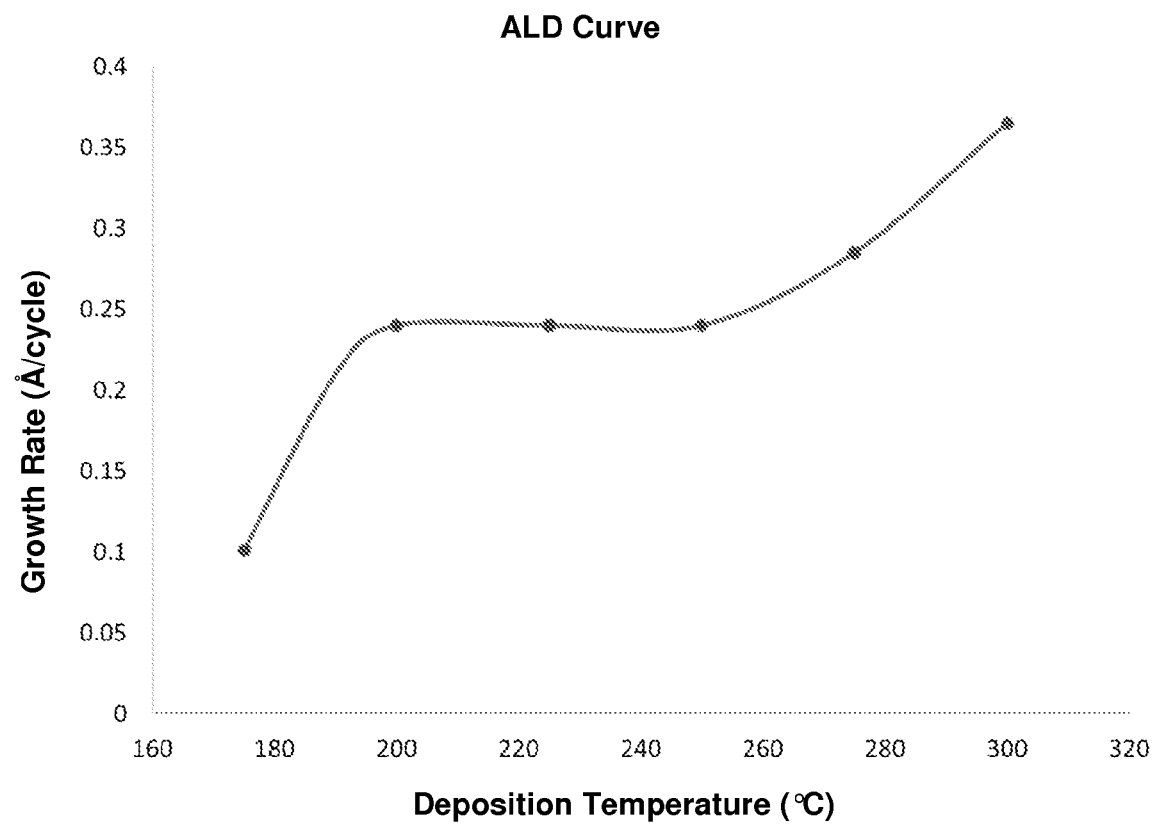
FIG. 21 is a graphical representation of Mo ALD curve data demonstrating growth rate vs. deposition temperature, for a Mo-containing film deposited on SiO$_2$ 1K, using water as a co-reactant. The molybdenum precursor and water pulse lengths were kept constant at 1.0 s.

As shown in FIG. 21, when water was used as the co-reactant (1.0 s pulse length), an ALD window was observed to be between ~195° C. and ~275° C., with a constant growth rate of 0.24 Å/cycle. Thus, the ALD window obtained with water as a co-reactant was significantly wider than when oxygen was used as a co-reactant.

Example 7

Atomic Layer Deposition Experiments with Ozone Co-Reactant

In all deposition experiments in this example, $CpMo(CO)_2(\eta^3$-2-methylallyl) was used as the molybdenum source and ozone was used as the co-reactant.

Figure 22:
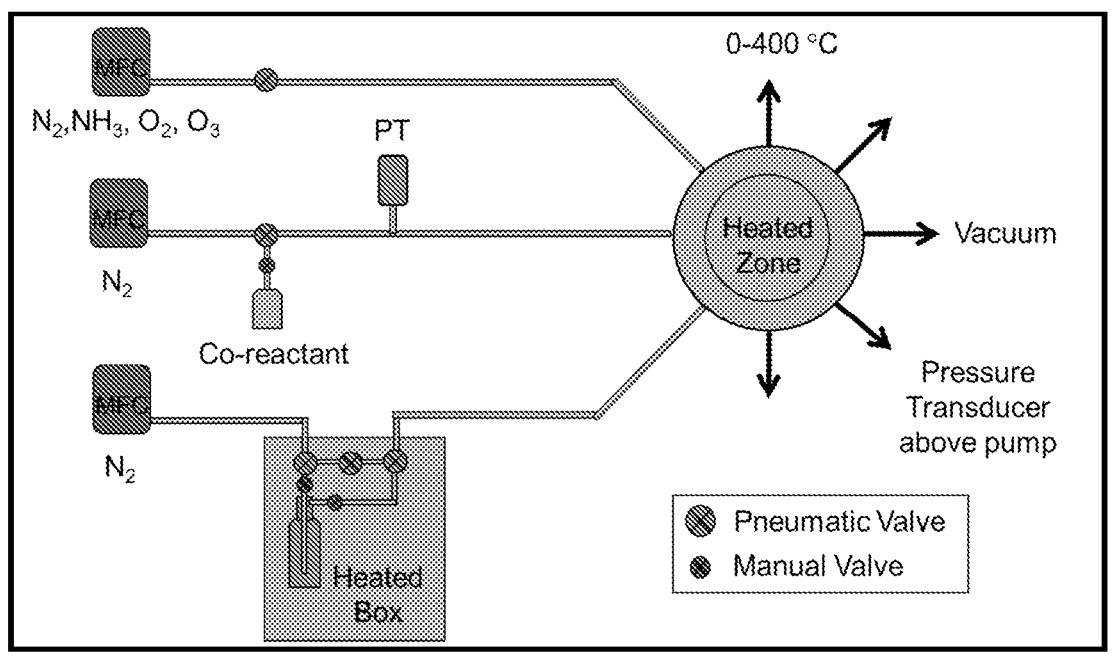
FIG. 22 is a schematic of a reactor used for ALD employing ozone as a co-reactant, according to some embodiments.

MeCpMo(CO)$_2$($\eta^3$-2-methylallyl), i-PrCpMo(CO)$_2$($\eta^3$-2-methylallyl), or MeCpMo(CO)$_2$($\eta^3$-2-tert-butylallyl) may also be used as the molybdenum source. FIG. 22 is a schematic of a reactor used for ALD experiments in this example. The Mo source was kept at 90° C. with a nitrogen carrier gas flow of 80 sccms during the experiments. The ozone co-reactant concentration was 260 g/Nm$^3$, at a flow rate of 60 sccms, and was pulsed for 1.0 s. In all the examples, the baseline reactor pressure was between 1.2 and 1.5 Torr. The substrates used were 100 nm SiO$_2$ on Si (SiO$_2$ 1 K) and hydrogen terminated Si(100) (Si(H-term)). Deposition occurred on all substrates in the examples described below. XPS spectra and cross sectional SEM micrographs for films deposited on Si were analyzed. As a measure of uniformity, film thicknesses were measured by cross-sectional SEM at many different points on the substrate.

Example 7A

Deposition of Mo by Atomic Layer Deposition with CpMo(CO)$_2$($\eta^3$-2-methylallyl), Using Ozone as a Co-Reactant Molybdenum oxide films were deposited by atomic layer deposition with the following parameters:
Substrate temperature: 150° C.
Co-reactant: Ozone
Nitrogen Purge Time: 5.0 s
Pulse Train: 1.0 s Mo precursor/5.0 s N$_2$ purge/1.0 s ozone/5.0 s N$_2$ purge
Total cycles: 1000

Figure 23:
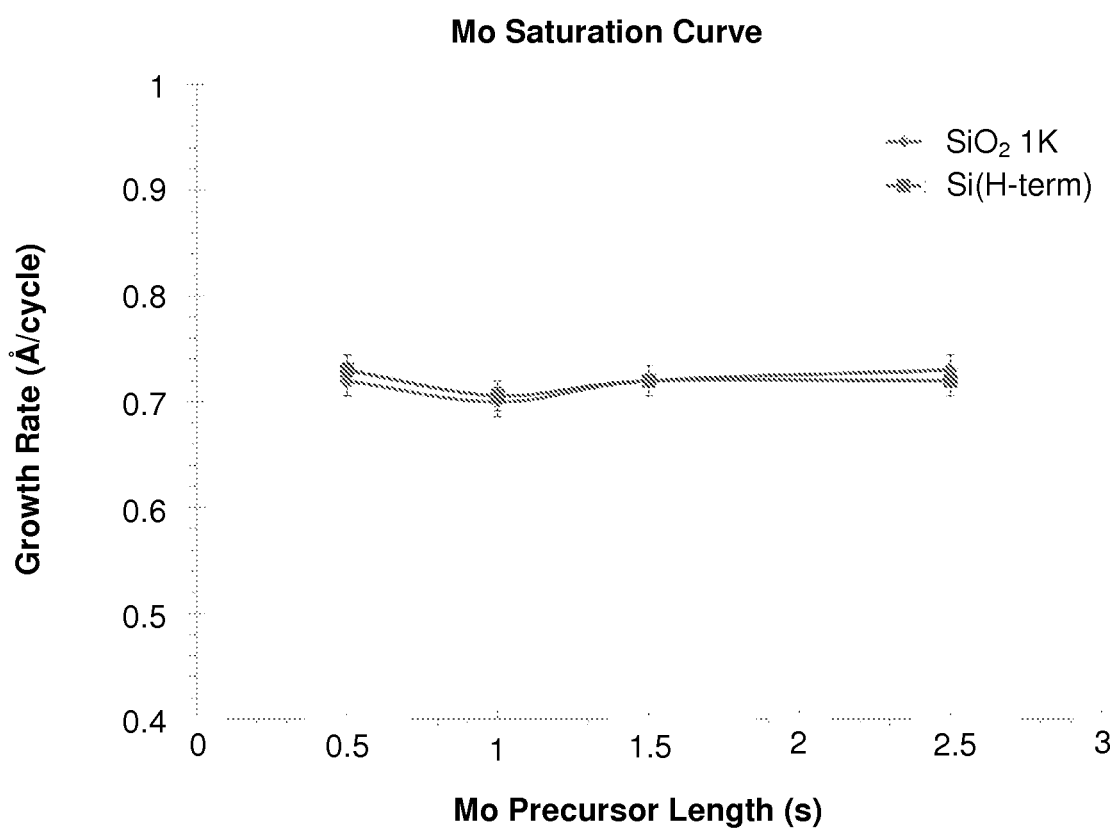
FIG. 23 is a graphical representation of Mo surface saturation data demonstrating growth rate vs. Mo precursor pulse length, on SiO$_2$ 1 K and hydrogen terminated Si(100).

FIG. 23 shows Mo surface saturation data demonstrating growth rate vs. Mo precursor pulse length, on two different substrate surfaces (SiO$_2$ 1 K and Si(H-term)), for CpMo(CO)$_2$($\eta^3$-2-methylallyl). In each case, the substrate temperature was 175° C. and ozone was pulsed for 1.0 s. FIG. 23 shows that, for each substrate, surface saturation occurs after 0.5 s, indicating that 175° C. film growth proceeds by ALD.

Figure 24:
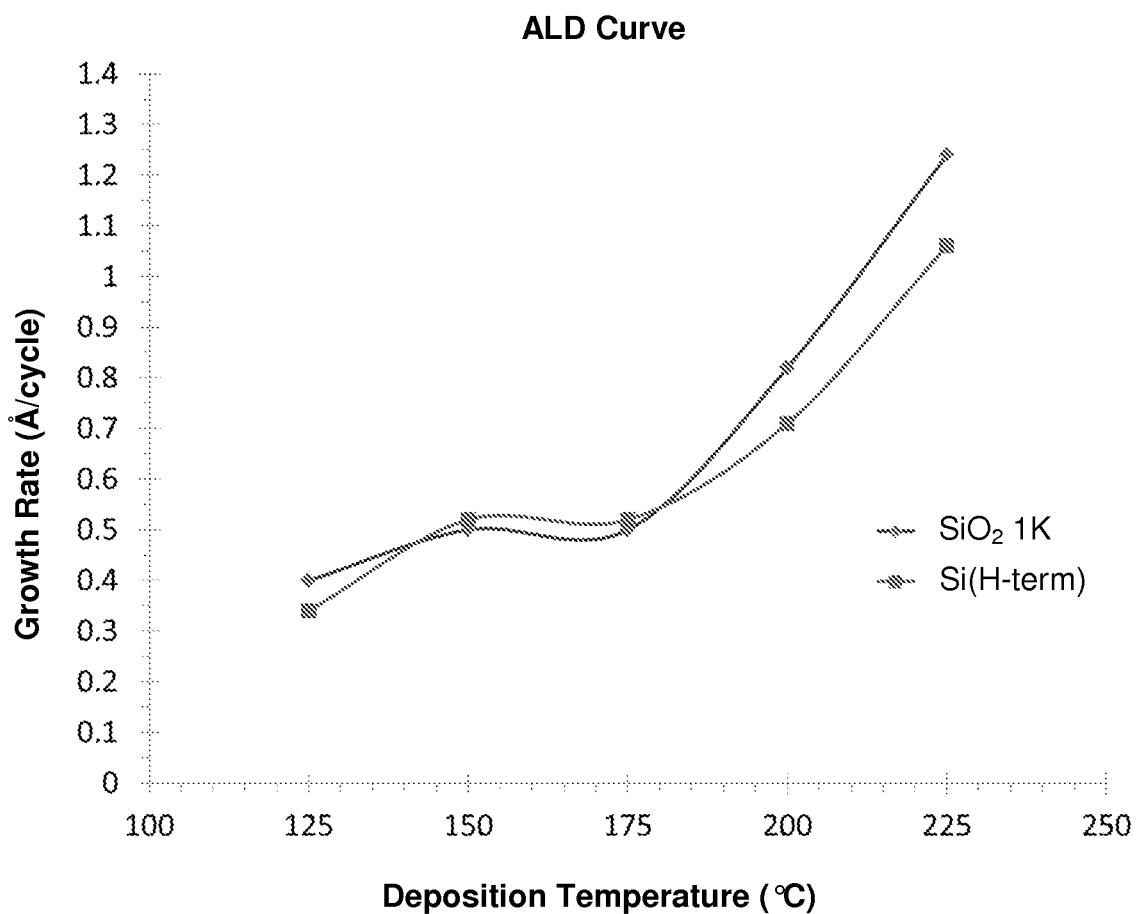
FIG. 24 is a graphical representation of Mo ALD curve data demonstrating growth rate vs. deposition temperature, on SiO$_2$ 1 K and hydrogen terminated Si(100).

FIG. 24 is a graphical representation of Mo ALD curve data demonstrating growth rate vs. deposition (substrate) temperature, on SiO$_2$ 1 K and Si(H-term), for CpMo(CO)$_2$($\eta^3$-2-methylallyl). In each case, the Mo precursor pulse length and ozone co-reactant pulse length were 2.0 s and 1.0 s, respectively. FIG. 24 shows an ALD window from ~150-175° C. with a constant growth rate of 0.52 Å/cycle (Si(H-term)) and 0.50 Å/cycle (SiO$_2$ 1 K).

Figure 25:
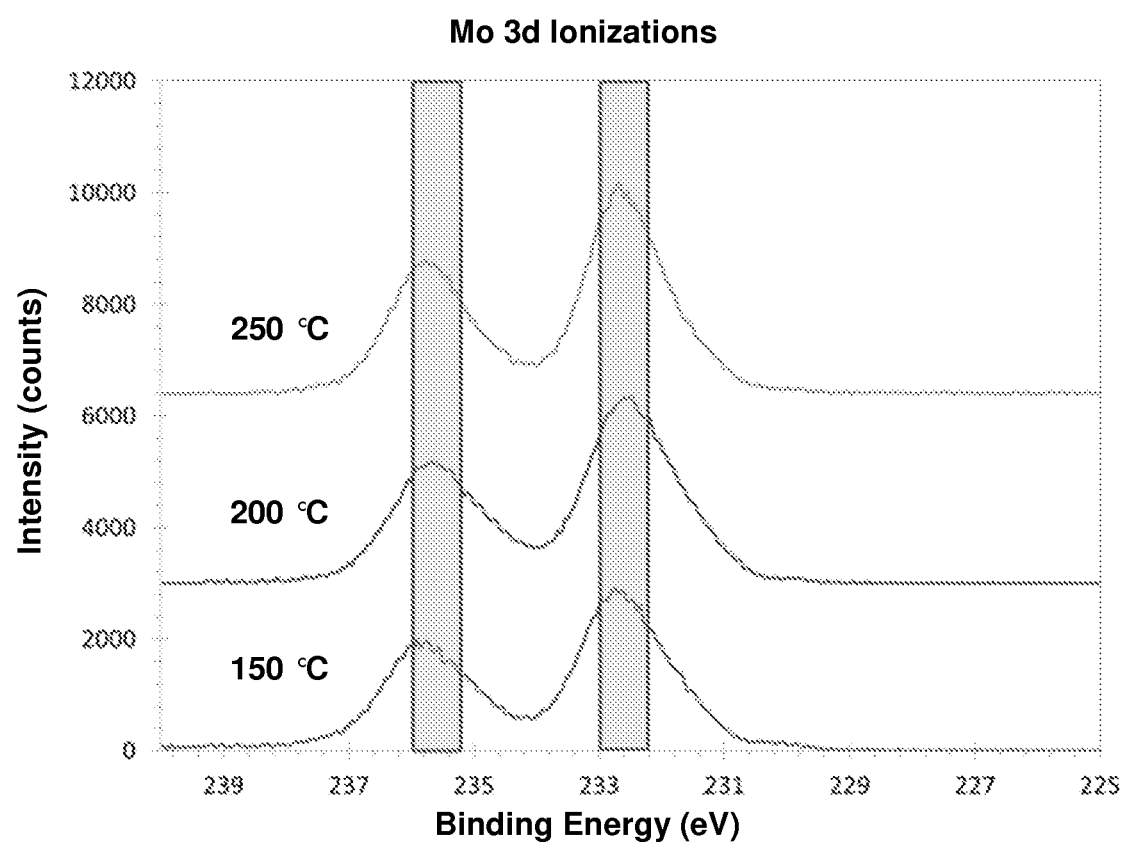
FIG. 25 is a graphical representation of Mo 3d ionization data demonstrating intensity vs. binding energy, at varying temperatures.
Figure 26:
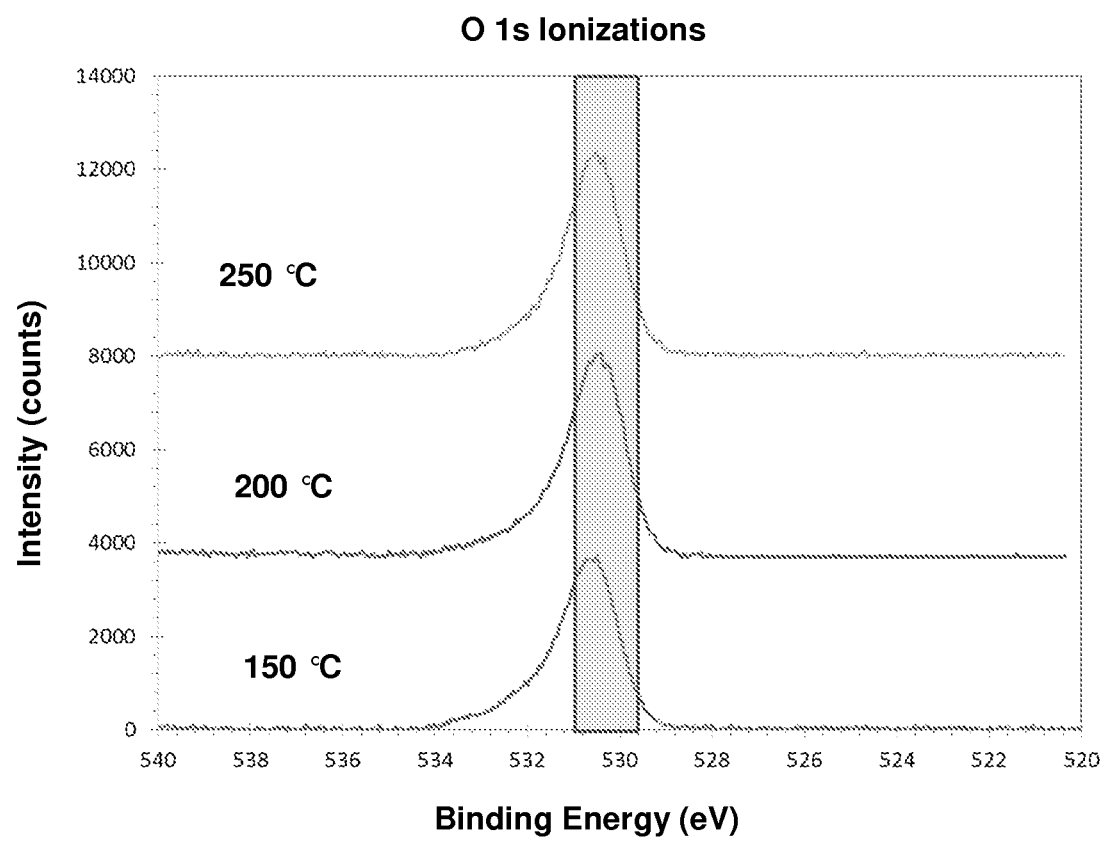
FIG. 26 is a graphical representation of O 1s ionization data demonstrating intensity vs. binding energy, at varying temperatures.

FIG. 25 is a graphical representation of Mo 3d ionization data demonstrating intensity vs. binding energy, at 150° C., 200° C., and 250° C., for CpMo(CO)$_2$($\eta^3$-2-methylallyl). FIG. 26 is a graphical representation of O is ionization data demonstrating intensity vs. binding energy, at varying temperature, for CpMo(CO)$_2$($\eta^3$-2-methylallyl). The shaded boxes in FIGS. 25 and 26 represent the literature values for ionizations belonging to Mo 3d 3/2 and Mo 3d 5/2 (FIG. 25), and O is (FIG. 26). For films sputtered for 2 minutes, the % at. carbon of the film was determined to be 5.6 (150° C.), 3.3 (200° C.), and 3.7 (250° C.) and O/Mo was determined to be 3.3/1 (150° C.), 3.1/1 (200° C.), and 3.0/1 (250° C.). Thus, the XPS data shows successful deposition of MoO$_3$ by ALD.

Figure 27:
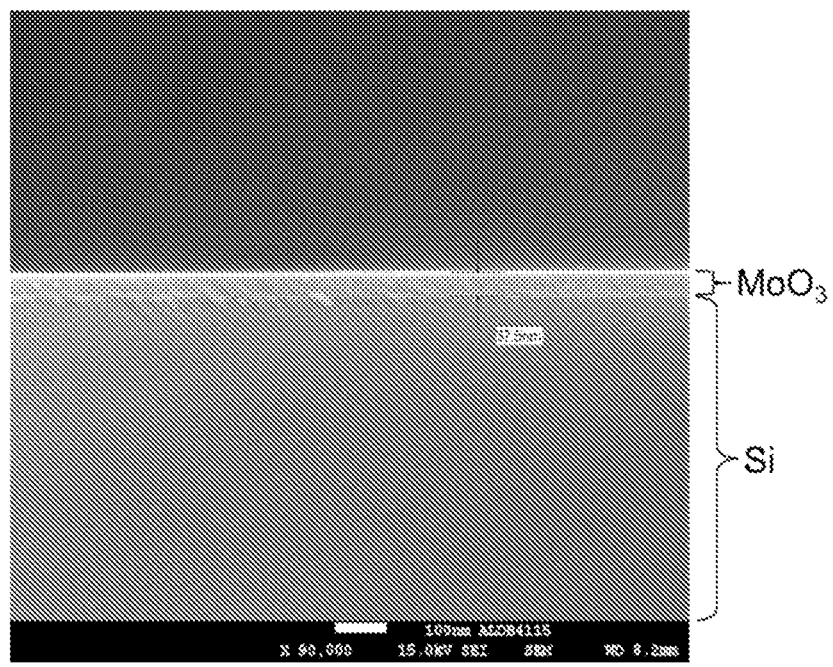
FIG. 27 is a SEM micrograph of a 37.5 nm $MoO_3$ film deposited on hydrogen terminated Si(100), with ozone as a co-reactant.

FIG. 27 is a SEM micrograph of a 37.5 nm MoO$_3$ film deposited on hydrogen terminated Si(100) at 175° C., using CpMo(CO)$_2$($\eta^3$-2-methylallyl) as the molybdenum source and ozone as a co-reactant.

Figure 28:
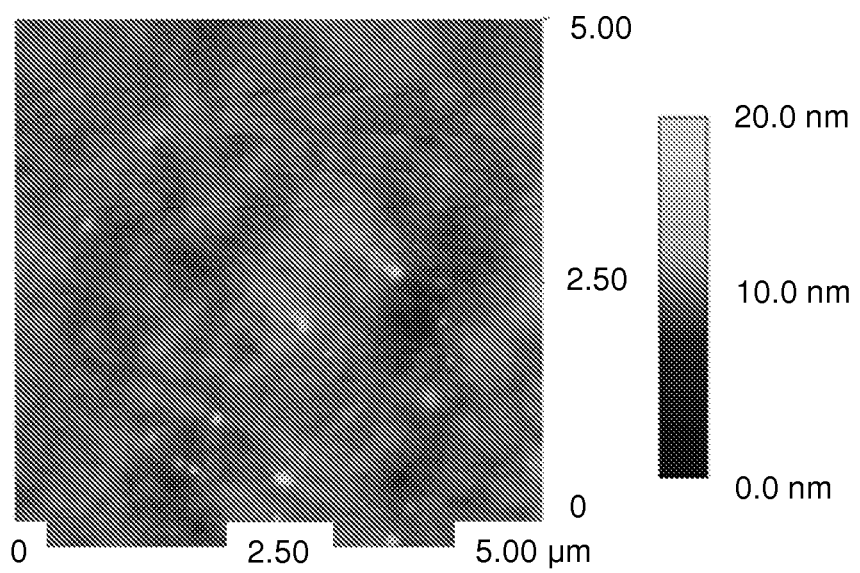
FIG. 28 is a AFM micrograph of a $MoO_3$ film deposited on hydrogen terminated Si(100) at 150° C., with ozone as a co-reactant.

FIG. 28 is a AFM micrograph of a MoO$_3$ film deposited on hydrogen terminated Si(100) at 150° C., using CpMo(CO)$_2$($\eta^3$-2-methylallyl) as the molybdenum source and ozone as a co-reactant. The RMS surface roughness was determined to be 0.72 nm.

Figure 29:
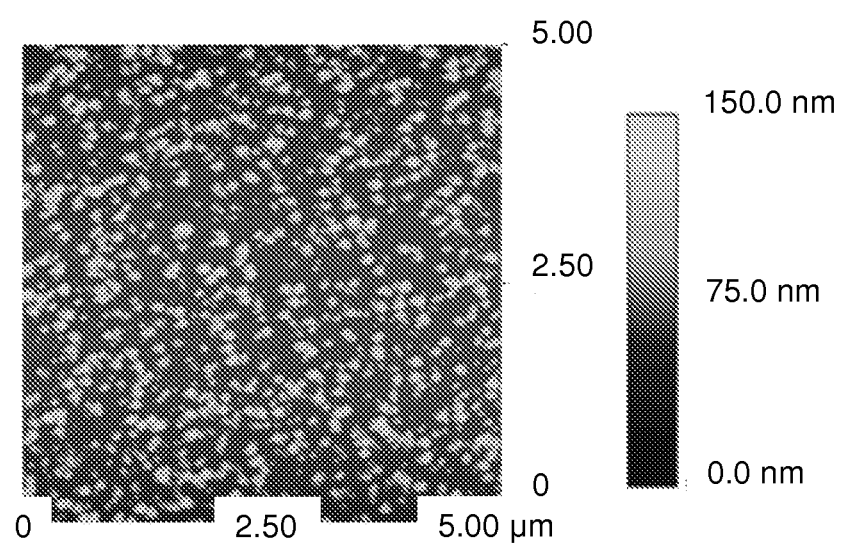
FIG. 29 is a AFM micrograph of a $MoO_3$ film deposited on hydrogen terminated Si(100) at 250° C., with ozone as a co-reactant.

FIG. 29 is a AFM micrograph of a MoO$_3$ film deposited on hydrogen terminated Si(100) at 250° C., using CpMo(CO)$_2$($\eta^3$-2-methylallyl) as the molybdenum source and ozone as a co-reactant. The RMS surface roughness was determined to be 15.74 nm.

A number of conclusions were made based upon the experiments in this example. First, low carbon containing MoO$_3$ thin films could be grown by ALD using CpMo(CO)$_2$($\eta^3$-2-methylallyl) and ozone at substrate temperatures of 125-225° C. An ALD window was observed between 150-175° C. Within the ALD window, the deposited films were smooth and featureless, indicative of ALD growth. MoO$_3$ films deposited above the ALD window (250° C.) were very rough, suggesting decomposition of the Mo precursor. CpMo(CO)$_2$($\eta^3$-2-methylallyl) (and structurally similar precursors) should be suitable for the deposition of molybdenum nitride, lower valent molybdenum oxides, and molybdenum sulfide.

All patents and publications cited herein are incorporated by reference into this application in their entirety and for all purposes as if fully set forth herein.

The words "comprise", "comprises", and "comprising" are to be interpreted inclusively rather than exclusively.

Further Embodiments

It is to be understood that the disclosure of the present invention extends to methods, products and systems according to the various aspects of the invention which comprise combinations of one or more features discussed herein by reference to certain embodiments of the invention with one or more further features discussed herein by reference to certain other embodiments of the invention.

Embodiment 1

An organometallic complex corresponding in structure to Formula I:

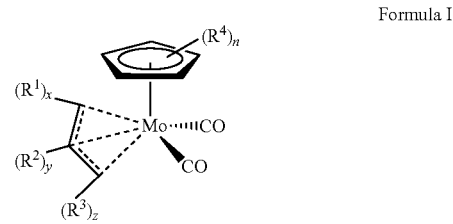

Formula I wherein
R$^1$ and R$^3$ are independently and at each occurrence alkyl;
R$^2$ is alkyl;
R$^4$ is independently and at each occurrence selected from the group consisting of alkyl, alkenyl, and alkynyl;
x and z are independently zero, 1, or 2;
y is zero or 1; and
n is zero to 5; wherein
  when n is zero, R$^1$ or R$^2$ or R$^3$, if present, is C$_2$-C$_8$-alkyl; and
  when n is 1, R$^1$ or R$^3$, if present, is C$_2$-C$_8$-alkyl.

Embodiment 2

The organometallic complex of Embodiment 1, wherein R$^1$, R$^3$ and R$^4$ are independently and at each occurrence C$_1$-C$_8$-alkyl; R$^2$ is alkyl, and when n is zero, $R^1$ or $R^2$ or $R^3$, if present, is $C_2$-$C_8$-alkyl; and when n is 1, $R^1$ or $R^3$, if present, is $C_2$-$C_8$-alkyl.

Embodiment 3

The organometallic complex of Embodiment 1 or 2, wherein n is zero or 1.

Embodiment 4

The organometallic complex of Embodiment 1 or 2, wherein n is 2 to 5.

Embodiment 5

The organometallic complex of any one of Embodiments 1-4, wherein x and z are zero.

Embodiment 6

The organometallic complex of any one of Embodiments 1-5, wherein y is 1.

Embodiment 7

The organometallic complex of Embodiment 1, wherein the complex is:

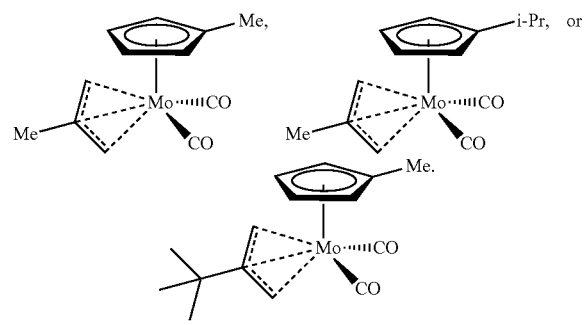

Embodiment 8

A method for forming a molybdenum-containing film by a vapor deposition process, the method comprising vaporizing at least one organometallic complex corresponding in structure to Formula I:

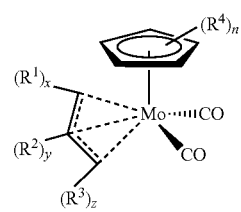

Formula I wherein
$R^1$ and $R^3$ are independently and at each occurrence alkyl;
$R^2$ is alkyl;
$R^4$ is independently and at each occurrence selected from the group consisting of alkyl, alkenyl, and alkynyl;

x and z are independently zero, 1, or 2;
y is zero or 1; and
n is zero to 5.

Embodiment 9

The method of Embodiment 8, wherein $R^1$, $R^3$ and $R^4$ are independently and at each occurrence $C_1$-$C_8$-alkyl; and $R^2$ is $C_1$-$C_8$-alkyl.

Embodiment 10

The method of Embodiment 8 or 9, wherein $R^1$, $R^3$ and $R^4$ are independently and at each occurrence $C_1$-$C_4$-alkyl; and $R^2$ is $C_1$-$C_4$-alkyl.

Embodiment 11

The method of any one of Embodiments 8-10, wherein n is zero or 1.

Embodiment 12

The method of any one of Embodiments 8-10, wherein n is 2 to 5.

Embodiment 13

The method of any one of Embodiments 8-12, wherein x and z are zero.

Embodiment 14

The method of any one of Embodiments 8-13, wherein y is zero.

Embodiment 15

The method of Embodiment 8, wherein the organometallic complex is selected from the group consisting of

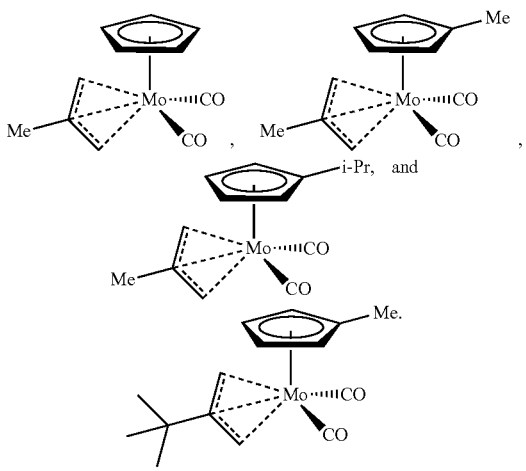

Embodiment 16

The method of any one of Embodiments 8-15, wherein the vapor deposition process is chemical vapor deposition, such as pulsed chemical vapor deposition or continuous flow chemical vapor deposition or liquid injection chemical vapor deposition.

Embodiment 17

The method of any one of Embodiments 8-15, wherein the vapor deposition process is atomic layer deposition, such as liquid injection atomic layer deposition or plasma-enhanced atomic layer deposition.

Embodiment 18

The method of any one of Embodiments 8-17, wherein the at least one organometallic complex is delivered to a substrate in pulses alternating with pulses of an oxygen source to form a metal oxide film.

Embodiment 19

The method of Embodiment 18, wherein the oxygen source is selected from the group consisting of $H_2O$, air, $O_2$, and ozone.

Embodiment 20

The method of any one of Embodiments 8-19, further comprising vaporizing at least one co-organometallic complex to form a metal oxide film.

Embodiment 21

The method of any one of Embodiments 8-20, further comprising vaporizing at least one co-reactant selected from the group consisting of hydrogen, hydrogen plasma, oxygen, air, water, ammonia, a hydrazine, a borane, a silane, ozone and a combination of any two or more thereof; preferably a hydrazine such as ($N_2H_4$) or N,N-dimethylhydrazine.

Embodiment 22

The method of any one of Embodiments 8-21, wherein the method is used for a DRAM or CMOS application.

What is claimed is:

1. An organometallic complex corresponding in structure to Formula I:

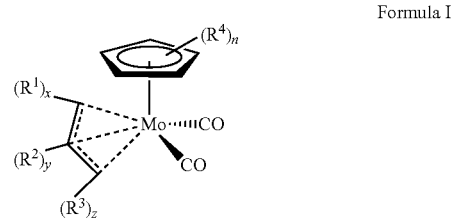

Formula I wherein
R$^1$ and R$^3$ are independently and at each occurrence alkyl;
R$^2$ is alkyl;
R$^4$ is independently and at each occurrence selected from the group consisting of alkyl, alkenyl, and alkynyl;
x and z are independently zero, 1, or 2;
y is zero or 1; and
n is 1 to 4; wherein
when n is 1, R$^1$ or R$^3$, if present, is $C_2$-$C_8$-alkyl.

2. The organometallic complex of claim 1, wherein R$^1$, R$^3$ and R$^4$ are independently and at each occurrence $C_1$-$C_8$-alkyl; R$^2$ is alkyl, and wherein
when n is 1, R$^1$ or R$^3$, if present, is $C_2$-$C_8$-alkyl.

3. The organometallic complex of claim 1, wherein n is 1.

4. The organometallic complex of claim 1, wherein n is 2 to 4.

5. The organometallic complex of claim 1, wherein x and z are zero.

6. The organometallic complex of claim 5, wherein y is 1.

7. The organometallic complex of claim 1, wherein the complex is:

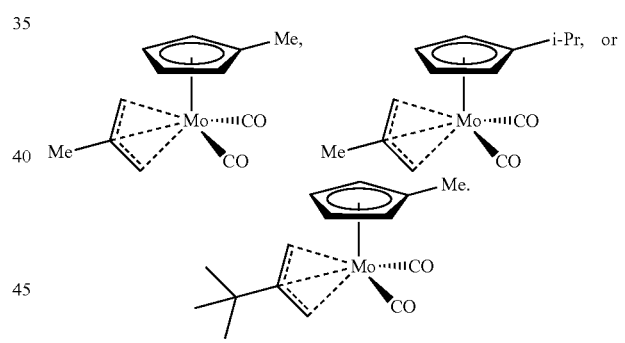

* * * * *